(12) United States Patent
Van Eijk et al.

(10) Patent No.: US 9,080,210 B2
(45) Date of Patent: Jul. 14, 2015

(54) HIGH THROUGHPUT SCREENING USING COMBINATORIAL SEQUENCE BARCODES

(75) Inventors: Michael Josephus Theresia Van Eijk, Wageningen (NL); Henricus Johannes Adam Van Der Poel, Wageningen (NL)

(73) Assignee: Keygene N.V., Wageningen (NL)

( * ) Notice: Subject to any disclaimer, the term of this patent is extended or adjusted under 35 U.S.C. 154(b) by 9 days.

(21) Appl. No.: 13/702,667

(22) PCT Filed: Jun. 8, 2011

(86) PCT No.: PCT/NL2011/050411
§ 371 (c)(1),
(2), (4) Date: Feb. 15, 2013

(87) PCT Pub. No.: WO2011/155833
PCT Pub. Date: Dec. 15, 2011

(65) Prior Publication Data
US 2013/0137587 A1 May 30, 2013

Related U.S. Application Data

(60) Provisional application No. 61/352,910, filed on Jun. 9, 2010, provisional application No. 61/457,005, filed on Dec. 6, 2010.

(51) Int. Cl.
*C12Q 1/68* (2006.01)
*C12P 19/34* (2006.01)

(52) U.S. Cl.
CPC ............ *C12Q 1/6869* (2013.01); *C12P 19/34* (2013.01); *C12Q 1/68* (2013.01); *C12Q 1/6855* (2013.01)

(58) Field of Classification Search
CPC .................................. C12Q 1/68; C12P 19/34
USPC .................................................. 435/6.1, 91.2
See application file for complete search history.

(56) References Cited

U.S. PATENT DOCUMENTS 4,683,195 A * 7/1987 Mullis et al. ................. 435/6.11
5,565,340 A * 10/1996 Chenchik et al. ............ 435/91.2
6,383,754 B1 * 5/2002 Kaufman et al. ............ 435/6.12
2006/0263789 A1 11/2006 Kincaid
2010/0069250 A1 * 3/2010 White et al. ..................... 506/4

FOREIGN PATENT DOCUMENTS

| CN | 101365803 A | 2/2009 |
| WO | WO 2007/037678 A2 | 4/2007 |
| WO | WO 2007/073171 A2 | 6/2007 |

OTHER PUBLICATIONS

International Search Report received in the parent application No. PCT/NL2011/050411, dated Dec. 23, 2011.
Gabriel, Christian, et al., "Rapid high-throughput human leukocyte antigen typing by massively parallel pyrosequencing for high-resolution allele identification", *Human Immunology*, vol. 70, No. 11, 2009, pp. 960-964.
Main, Bradley, et al., "Allele-specific expression assays using Solexa", *BMC Genomics*, vol. 10, 2009, pp. 1-9.
Rigola, Diana, et al., "High-throughput detection of induced mutations and natural variation using KeyPoint technology", *PLOS One*, vol. 4, No. 3, 2009, pp. 1-9.
Wang, Zhen, et al., "CLIP: Construction of cDNA libraries for high-throughput sequencing from RNAs cross-linked to proteins in vivo", *Methods*, vol. 48, No. 3, 2009, pp. 287-293.
Galan, et al., "A 454 multiplex sequencing method for rapid and reliable genotyping of highly polymorphic genes in large-scale studies", BMC Genomics, 2010, 11:296.
Translation of Chinese Notification of First Office Action for Application No. 201180028072.1 dated Dec. 26, 2013.

\* cited by examiner

*Primary Examiner* — Ardin Marschel
(74) *Attorney, Agent, or Firm* — Sunit Talapatra; Foley & Lardner LLP

(57) ABSTRACT

The invention involves methods and uses of a combination of at least two nucleotide sequence identifiers in the preparation of a sample DNA for high throughput sequencing. Accordingly, in the high throughput sequencing a plurality of prepared sample DNAs, each preparation of a sample DNA comprises a unique combination of the at least two nucleotide sequence identifiers wherein a first nucleotide sequence identifier is selected from a group of nucleotide sequence identifiers and a second nucleotide sequence identifier is selected from the group of nucleotide sequence identifiers.

13 Claims, 12 Drawing Sheets

Figure 2

(1) 5'════════════════════════5'

Figure 1:
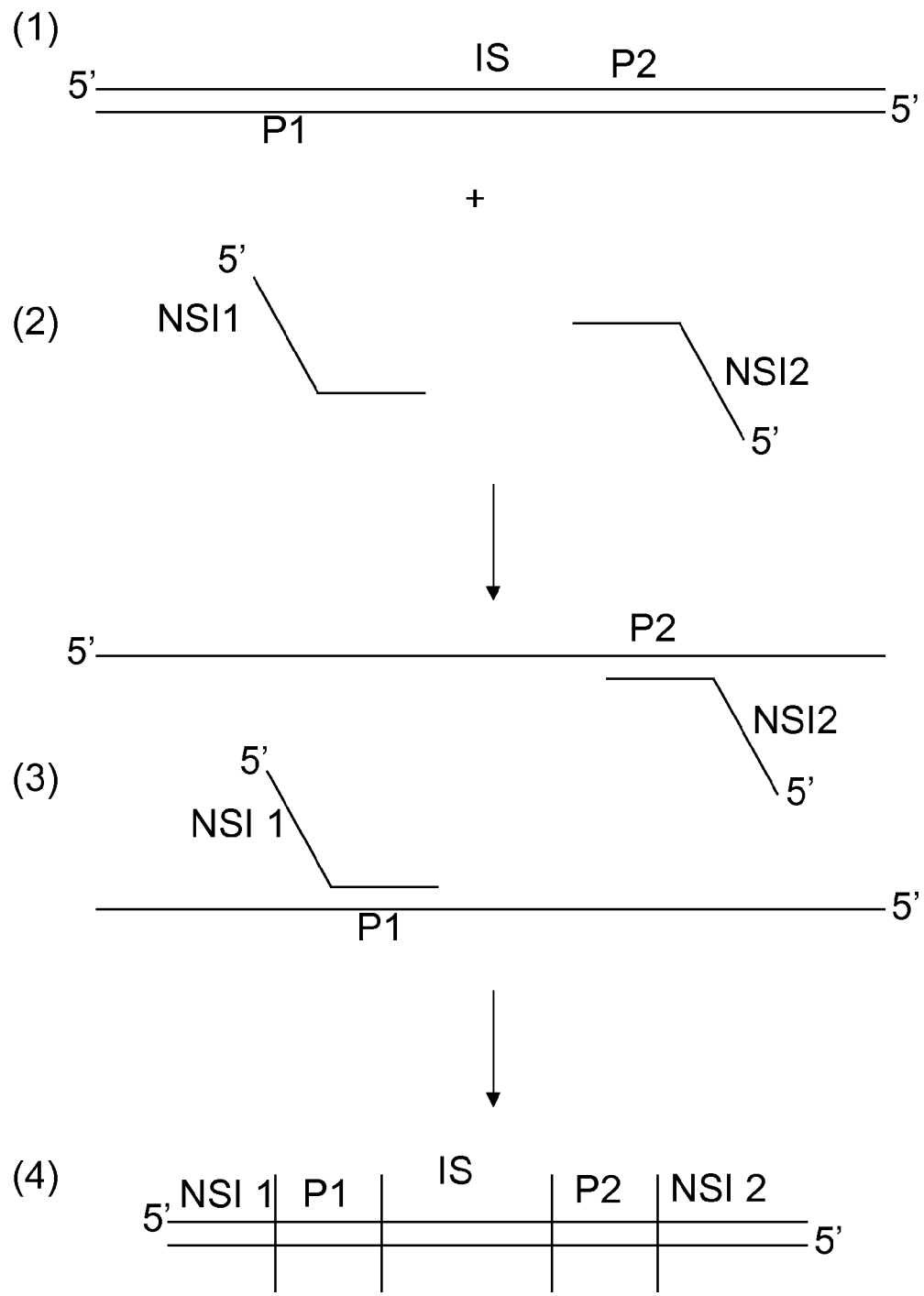

(2) 5'═══5'  5'══════5'       5'═════════5'
              +

(3) 5'═══5'                    5'═══5'
    NSI1                        NSI2

IS
(4) 5'────────────────5'
    NSI1           NSI2

A

B

A

P5  BC1  EcoRI  MseI  BC2  P7

B

P5  BC1  EcoRI  B  BC2  P7

HIGH THROUGHPUT SCREENING USING COMBINATORIAL SEQUENCE BARCODES

CROSS-REFERENCE TO RELATED PATENT APPLICATIONS

This application is the U.S. National Phase of PCT/NL2011/050411, filed Jun. 8, 2011, which claims priority to U.S. Provisional Patent Application 61/352,910, filed Jun. 9, 2010 and U.S. Provisional Patent Application No. 61/457,005, filed Dec. 6, 2010, which is incorporated herein by reference in entirety.

FIELD OF THE INVENTION

The present invention relates to the field of molecular biology, in particular to the preparation of sample DNA for sequencing methods. More specifically, the present invention relates to the use of nucleotide sequence identifiers for high throughput sequencing.

BACKGROUND OF THE INVENTION

The high demand for low-cost sequencing has driven the development of high-throughput sequencing technologies. In such technologies, millions of sequences are produced in parallel. For example, 454 Life Sciences, now Roche Applied Sciences, developed a high throughput sequencing technology of a sample DNA involving the steps of fragmenting DNA, ligating adapters to the DNA fragments, capturing single DNA fragments with a bead coated with primers, amplifying each DNA fragment on a bead inside water droplets in oil (emulsion PCR), and subsequently loading each bead in a picoliter-well and sequence each amplified DNA fragment with pyrosequencing. In general, high throughput sequencing technologies involve the ligation of adapters to DNA fragments, which adapters may comprise primer binding sites used for capture, amplification and/or sequencing of the DNA fragments. Because large numbers of sequences can be produced, samples from different origin are often combined in a single high throughput sequencing run. In order to trace back the origin of each sample from a pool of samples, current high throughput sequencing applications rely on the use of nucleotide sequence identifiers. The term nucleotide sequence identifier (NSI, (sequence-based barcode or sequence index are terms that are interchangeable and have the same meaning. A nucleotide sequence identifier is a particular nucleotide sequence that is used as an identifier. A nucleotide sequence identifier is included in the adapter downstream of the primer binding site such that when sequenced from the primer binding site, the nucleotide sequence of the identifier sequence is determined. Different adapters comprising different nucleotide sequence identifiers are ligated to different samples, after which the samples can be pooled. When the sequences are determined of the pooled samples, the nucleotide sequence identifier is sequenced along with part of the sequence of the fragment to which the adapter is ligated. The presence or absence of the nucleotide sequence identifier thus determines the presence or absence of a sample DNA in the pool. The sequence of the internal sequence that is sequenced along with the nucleotide sequence identifier further enables to assign that sequence to a particular sample from which it originated, as the nucleotide sequence identifier serves to identify the sample DNA origin.

For example, in the high throughput sequence system developed by Roche, the Genome Sequencer FLX system, multiplexed identifier sequences (MIDs) are used. The MIDs are 10-mer sequences that are incorporated into the adapters to assign sequence reads to individual samples. Over 100 different MIDs are currently in use (454 Life Science Corp (2009) Technical Bulletin No. 005-2009). Similar nucleotide sequence identifiers are available for other sequencing systems.

Methods, wherein nucleotide sequence identifiers are incorporated in the 5'-end of a primer, are e.g. described by Rigola et al. PLoS ONE. 2009; 4(3): e4761 and in WO 2007/037678. Typically, the nucleotide sequence identifiers do not have significant complementarity with the target sequence. A primer thus comprises at the 5'-end a section comprising a nucleotide sequence identifier and at the 3'-end the sequence which is complementary to the target sequence. When a sample is amplified with a primer pair of which a primer comprises a nucleotide sequence identifier, the amplicon will include the nucleotide sequence identifier. When samples are subsequently pooled, and subjected to high-throughput sequencing methods, the nucleotide sequence identifier will serve to identify the origin of the sequenced amplicon. Hence, the origin of the amplicon is determined by determining the nucleotide sequence identifier. Concomitantly, the internal sequence which has been amplified and is also sequenced along with the nucleotide sequence identifier can also be traced back to the samples from which they originate.

In both scenarios, an adapter or primer which comprises a nucleotide sequence identifier, the concept is the same, namely to determine the sample origin of sequences produced using high throughput sequencing platforms from a plurality of DNA samples that have been multiplexed, e.g. combined or pooled, somewhere in the sample preparation process.

SUMMARY OF THE INVENTION

The capacity of high throughput sequencing technologies capacity has been increasing an order of magnitude per two year period since its introduction. With high throughput sequencing enabling the multiplexing of an increasingly larger number of samples, the number of unique adapters or primers that is required to identify the origin of the samples is also increasing. Although the usage of 100 different primers or adapters may already be challenging, when the number would increase to 1000, it may become a bottleneck. Hence it is desirable that the number of primers and/or adapters that has to be used can be reduced because this may simplify sample preparation, may reduce the workload, may optimize technical performance and can reduce costs. The current invention enables to reduce the number of different primers and/or adapters required. The number could be reduced by the use of so called "split barcodes". Split barcodes according to the invention are nucleotide sequence identifiers that are present on at least two adapters and/or primers. A sample DNA (or combination of sample DNAs) is prepared using e.g. a primer pair and/or a pair of adapters, each primer or adapter of the pair comprising a nucleotide sequence identifier. The amplicon or adapter ligated DNA fragment that is produced comprises the at least two nucleotide sequence identifiers. For each different sample a unique combination of nucleotide identifiers can be used. The combination of nucleotide sequence identifiers, together also indicated as the split barcode, serves as the identifier.

BRIEF DESCRIPTIONS OF THE DRAWINGS

FIG. 1. Method for preparation of an amplicon from a sample DNA with two nucleotide sequence identifiers. A sample DNA is provided (1) comprising an internal sequence (IS) flanked by two primer binding sites (P1 and P2), as well as a pair of amplification primers (2) comprising sequences complementary to a primer binding site at the 3'-end and nucleotide sequence identifiers (NSI1 and NSI2) 5' thereof. The sample DNA is amplified with the amplification primers (3), resulting in an amplicon with two nucleotide sequence identifiers on either side. (5' indicates the 5'-end of a nucleotide strand, the 3'end has no annotation).

FIG. 2. Method for preparation of an adapter ligated DNA fragment from a sample DNA with two nucleotide sequence identifiers.
A sample DNA is provided (1), which is fragmented providing DNA fragments (2), a pair of adapters comprising a first and second NSI (NSI1 and NSI2) is provided (3) which are ligated to both ends of a DNA fragment, resulting in an adapter ligated DNA fragment (4). (5' indicates the 5'-end of a nucleotide strand).

Figure 3:
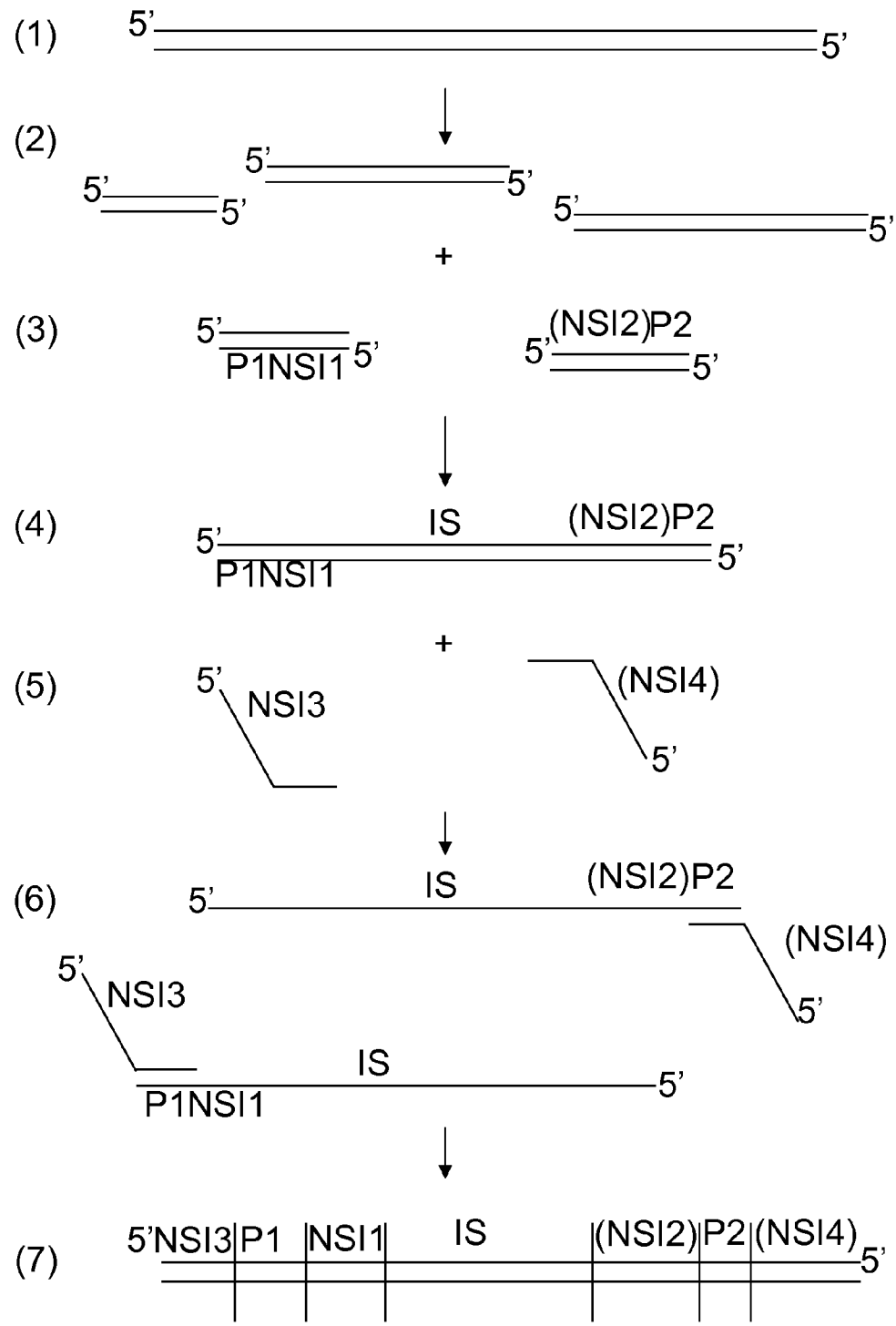

FIG. 3. Method for preparation of an amplified adapter ligated DNA fragment from a sample DNA with 2, 3 or 4 nucleotide sequence identifiers.
A sample DNA is provided (1), which is fragmented providing DNA fragments (2), a pair of adapters is provided of which at least one comprises an NSI (NS1 and optionally (NS2)) and both comprise a primer binding site (P1 and P2), which are ligated with a DNA fragment (3), i.e. internal sequence (IS), resulting in an adapter ligated DNA fragment (4) comprising the primer binding sequences on both ends of the adapter ligated DNA fragments. A pair of amplification primers is provided (5) each comprising at the 3'-end a sequence complementary to a sequence primer binding site, and at least one amplification primer comprises at the 5'-end a nucleotide sequence identifier (NSI3 or optionally (NSI4)). The adapter ligated DNA fragment is amplified with the pair of amplification primers (6). The result (7) being an amplified adapter ligated DNA fragment comprising at least two NSIs. The at least two NSIs can be flanking the IS, and/or the at least two NSIs can be on the same side of the IS. (5' indicates the 5'-end of a nucleotide strand; the parentheses indicate that the inclusion of the second and/or fourth NSI may be optional in this method).

Figure 4:
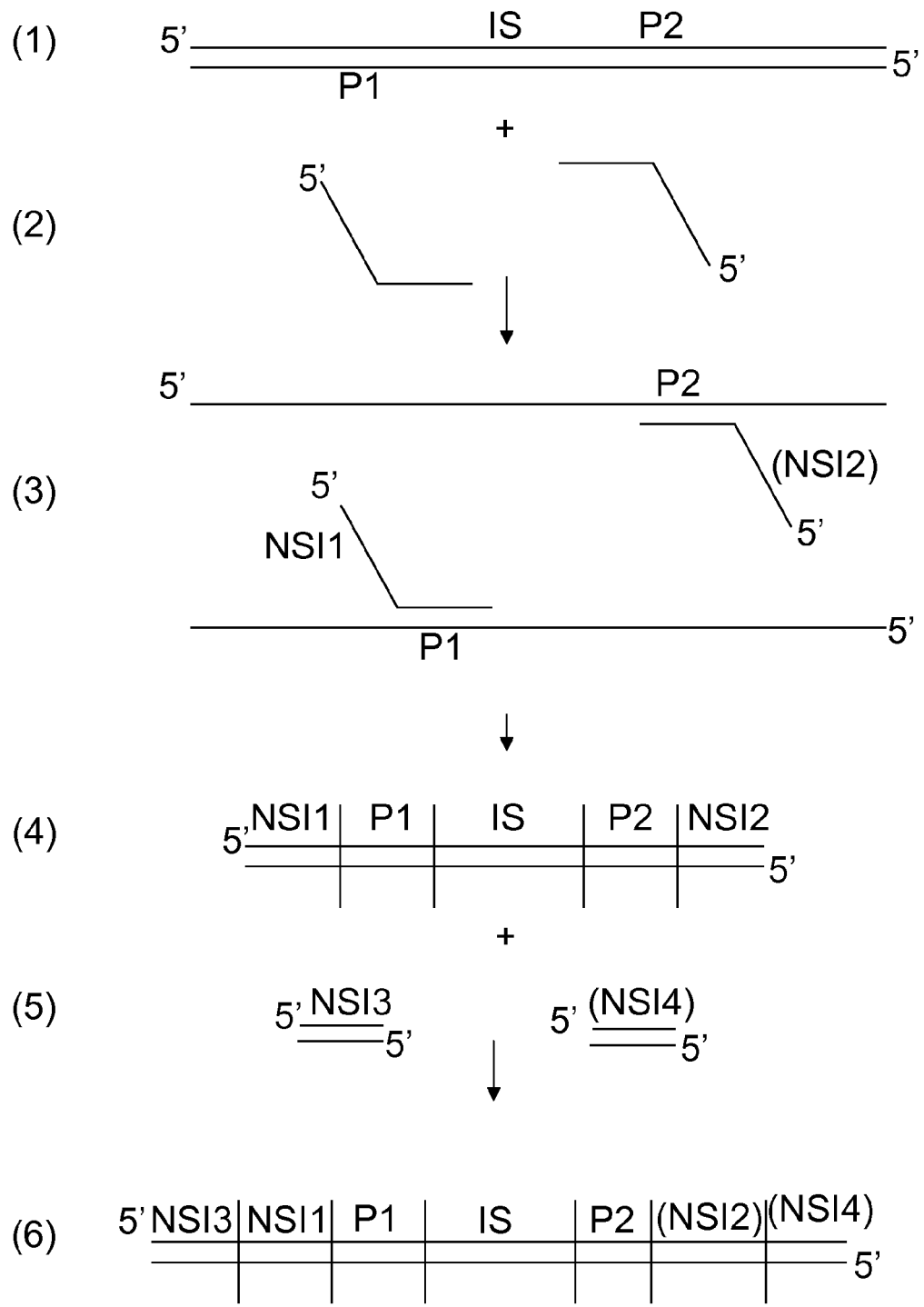

FIG. 4. Method for a preparation of an adapter ligated amplicon from a sample DNA with two, three or four nucleotide sequence identifiers. A sample DNA is provided (1) comprising an internal sequence (IS) flanked by two primer binding sites (P1 and P2), as well as a pair of amplification primers (2) comprising at the 3'-end sequences complementary to a primer binding site and at least one of the primers comprising a nucleotide sequence identifier (NSI1 and optional (NSI2)) at the 5'-end. The sample DNA is amplified with the amplification primers (3), resulting in an amplicon with at least one nucleotide sequence identifier (4). A pair of adapters is provided comprising a third and optional fourth nucleotide NSI (NSI3 and optional (NSI4)) which are ligated to either ends of the amplicon thereby providing an adapter ligated amplicon (6). The at least two NSIs can be flanking the IS, and/or the at least two NSIs can be on the same side of the IS. (5' indicates the 5'-end of a nucleotide strand; the parentheses indicate that the inclusion of the second and/or fourth NSI may be optional in this method).

Figure 5:
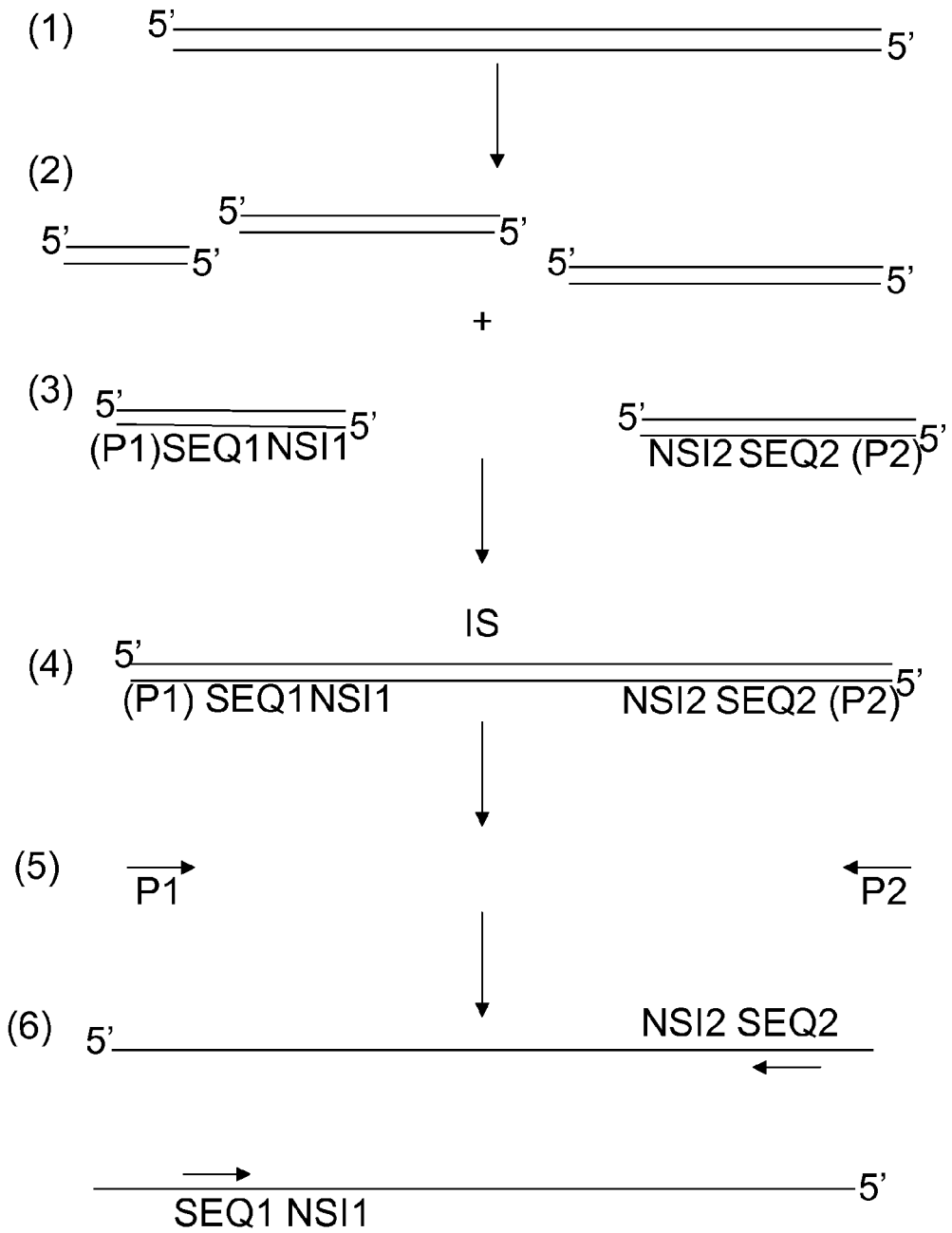

FIG. 5. Method for determining the two nucleotide sequence identifiers sequences of an adapter ligated DNA fragment.
A sample DNA is provided (1), which is fragmented providing DNA fragments (2), a pair of adapters comprising a first and second NSI (NSI1 and NSI2) is provided (3) which are ligated to either ends of a DNA fragment, resulting in an adapter ligated DNA fragment (4). The adapters each comprise a sequencing primer binding site (SEQ1 and SEQ2), and optionally each comprise an amplification primer binding site ((P1) and (P2)). The order of the sites present in an adapter is: (P)-SEQ-NSI, e.g. (P1)-SEQ1-NSI1. The side of the adapter that is ligated to the DNA fragment is the side comprising the NSI. The adapter ligated DNA fragment may optionally be amplified with primers directed to the primer binding sites (4). Each strand of the adapter ligated DNA fragment may serve as a template for a sequencing reaction. One template strand used is represented as follows: 3'-(P1)-SEQ1-NSI1-IS-NSI2(P2)-SEQ2-5', for which a sequencing primer is used against SEQ1. Sequencing primers are provided such that from each template from SEQ1 or SEQ2 the NSI sequence(s) are determined. The sequences may be determined separately. The sequences may be determined consecutively, e.g. such as in paired-end sequencing. (5' indicates the 5'-end of a nucleotide strand).

Figure 6:
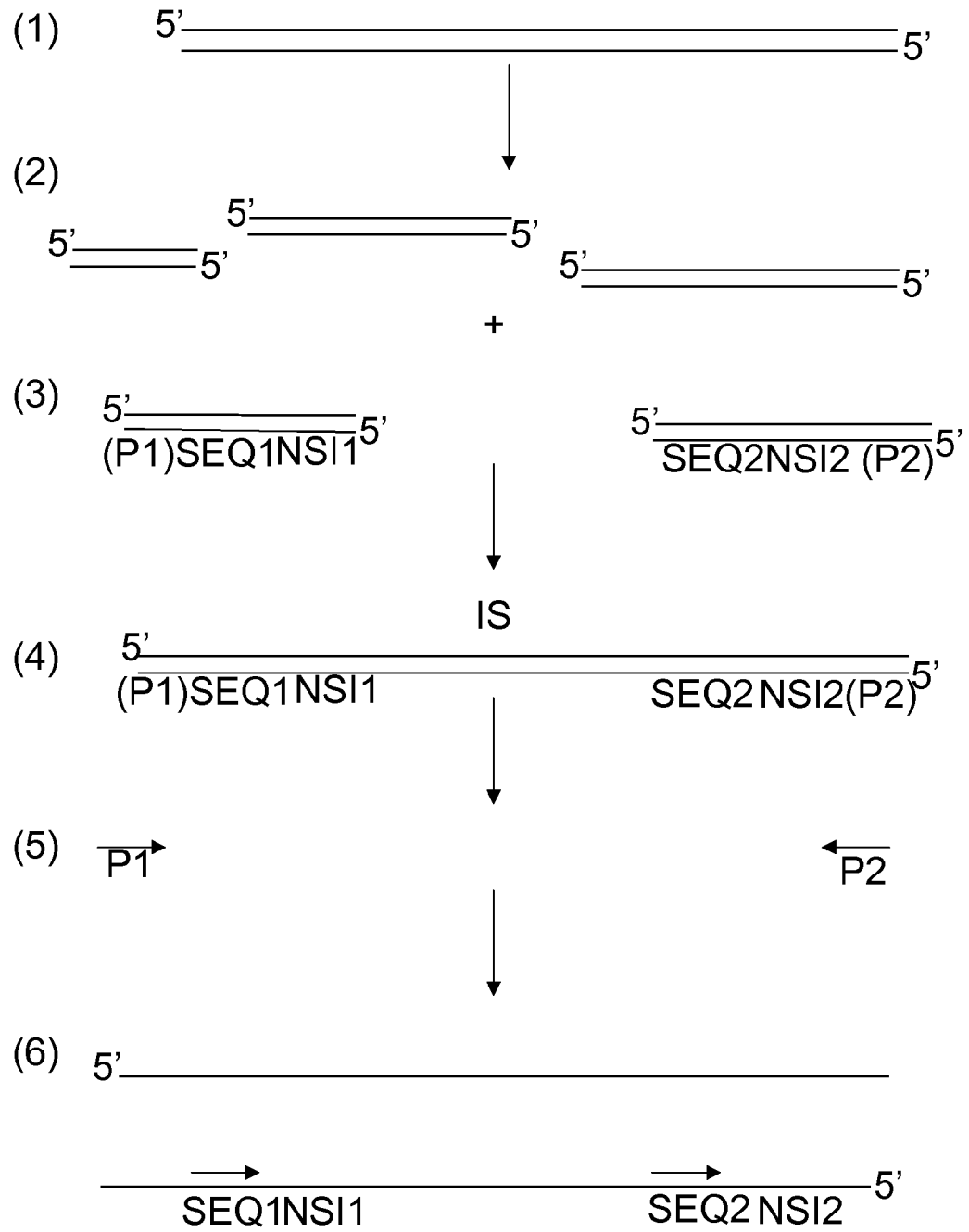

FIG. 6. Method for determining the two nucleotide sequence identifiers sequences of an adapter ligated DNA fragment: single-read double-tagging.
A sample DNA is provided (1), which is fragmented providing DNA fragments (2), a pair of adapters comprising a first and second NSI (NSI1 and NSI2) is provided which are ligated to either ends of a DNA fragment (3), resulting in an adapter ligated DNA fragment (4). The adapters each comprise a sequencing primer binding site (SEQ1 or SEQ2), and optionally each comprise an amplification primer binding site ((P1) or (P2)). The order of the sites present in the two adapters is (P1)-SEQ1-NSI1 and SEQ2-NSI2-(P2). The adapters are ligated to the DNA fragment such that the (P1) and (P2) sites are the outward sites of the adapter ligated DNA fragment (4), which may optionally be amplified with primers directed thereto (5). One strand of the adapter ligated DNA fragment may serve as a template for sequencing using the SEQ1 and SEQ2 sequencing primer binding sites in two different sequencing reactions, i.e. using the corresponding different sequencing primers. The template strand used is represented as follows: 3'-(P1)-SEQ1-NS1'-IS-SEQ2-NSI2-(P2)-5'. (5' indicates the 5'-end of a nucleotide strand).

Figure 7:
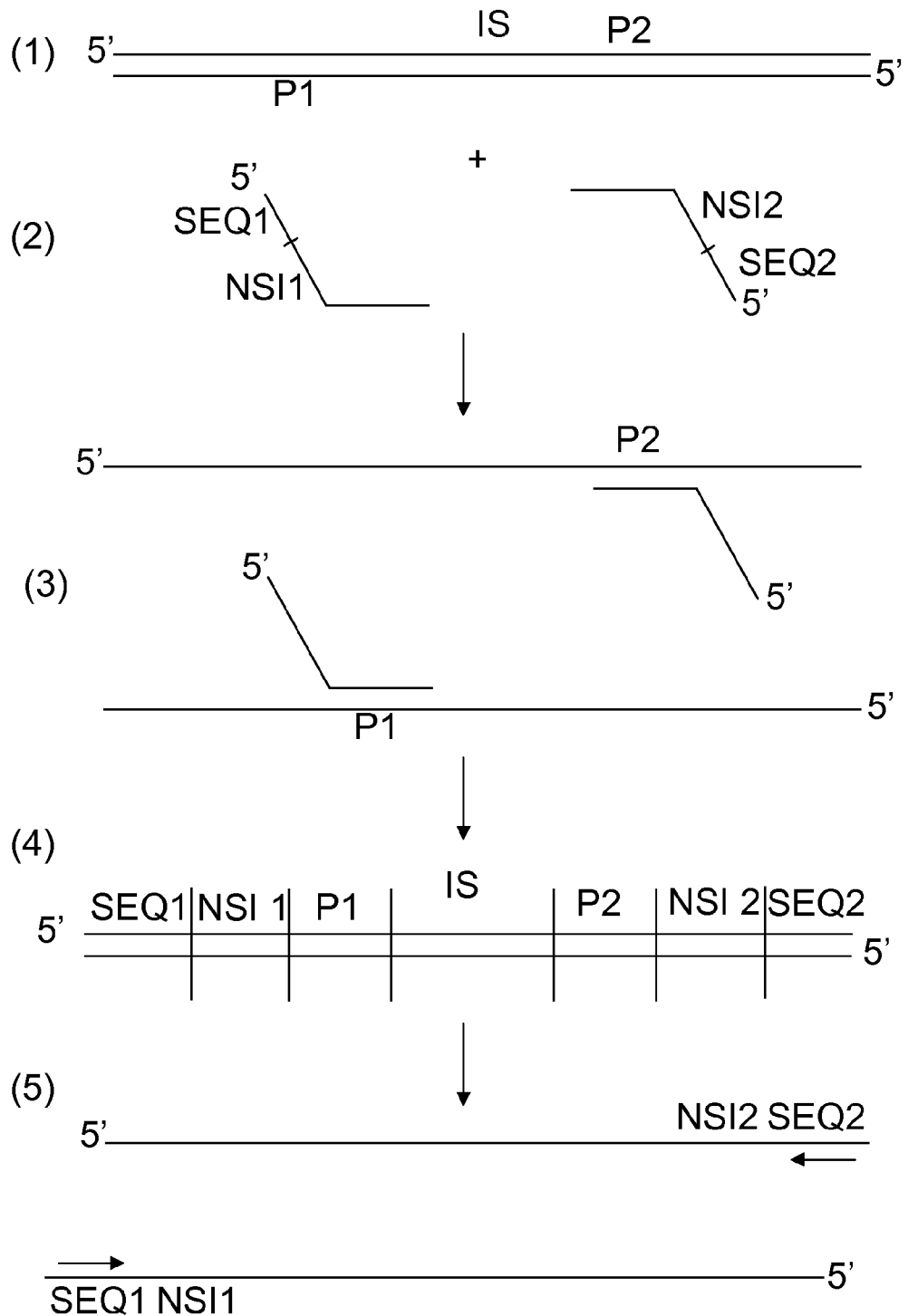

FIG. 7. Method for determining the sequence of two nucleotide sequence identifiers of an amplicon from a sample DNA. A sample DNA is provided (1) comprising an internal sequence (IS) flanked by two primer binding sites (P1 and P2), as well as a pair of amplification primers (2) comprising at the 3'-end sequences complementary to a primer binding site and sequencing primer binding sites (SEQ) at the 5' ends. In between, in the amplification primers, nucleotide sequence identifiers are located. The sample DNA is amplified with the amplification primers (3), resulting in an amplicon with two nucleotide sequence identifiers on either side, with on the outer ends of the amplicon the two SEQs (SEQ1 and SEQ2). Each strand of the amplicon may serve as a template for a sequencing reaction. One template strand used is represented as follows: 3'-SEQ1-NSI1-P1-IS-P2-NS12-SEQ2-5', for which a sequencing primer is used against SEQ1. Sequencing primers are provided such that from each template the NSI sequence(s) are determined. The sequences may be determined separately. The sequences may be determined consecutively, e.g. such as in paired-end sequencing. (5' indicates the 5'-end of a nucleotide strand).

Figure 8:
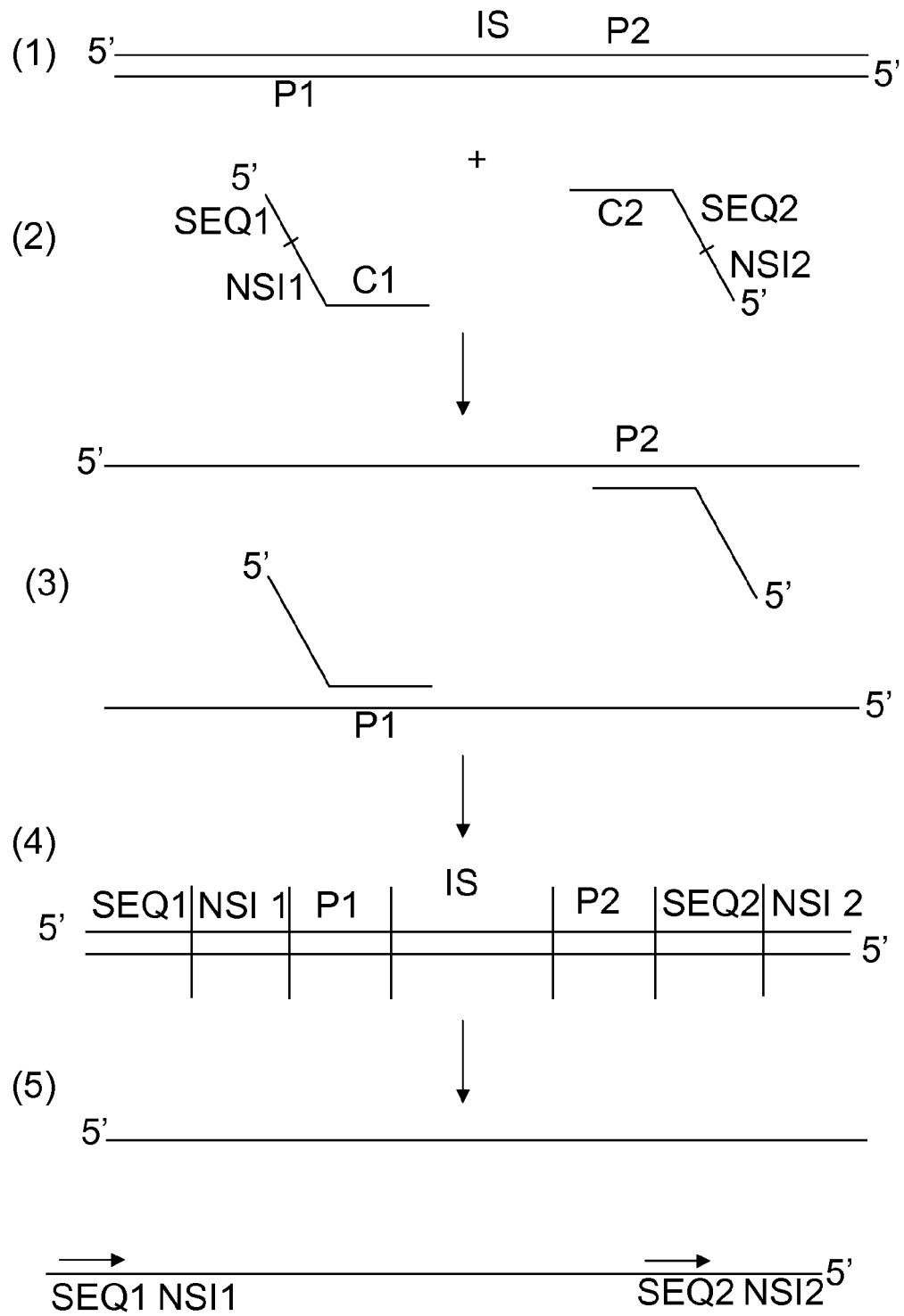

FIG. 8. Method for determining the sequence of two nucleotide sequence identifiers of an amplicon from a sample DNA: single-read double-tagging. A sample DNA is provided (1) comprising an internal sequence (IS) flanked by two primer binding sites (P1 and P2), as well as a pair of amplification primers (2) comprising sequences complementary to a primer binding site at the 3'-end (C1 or C2). The primers comprise in addition NSIs and sequencing primer binding sites, the different primers comprising the different sites/sequences being represented as follows: 5'-SEQ1-NSI1-C1 and C2-SEQ2-NSI2-5'. The sample DNA is amplified with the amplification primers (3), resulting in an amplicon with a nucleotide sequence identifier on each side, with on one outer end of the amplicon SEQ1 and on the other outer end NSI2 (4). One strand of the amplicon may serve as a template for sequencing using the SEQ1 and SEQ2 sequencing primer binding sites in two different sequencing reactions, i.e. using the corresponding different sequencing primers. The template strand used is represented as follows: 3'-SEQ1-NSI1-P1-IS-P2-SEQ2-NSI2-5'. (5' indicates the 5'-end of a nucleotide strand).

Figure 9:
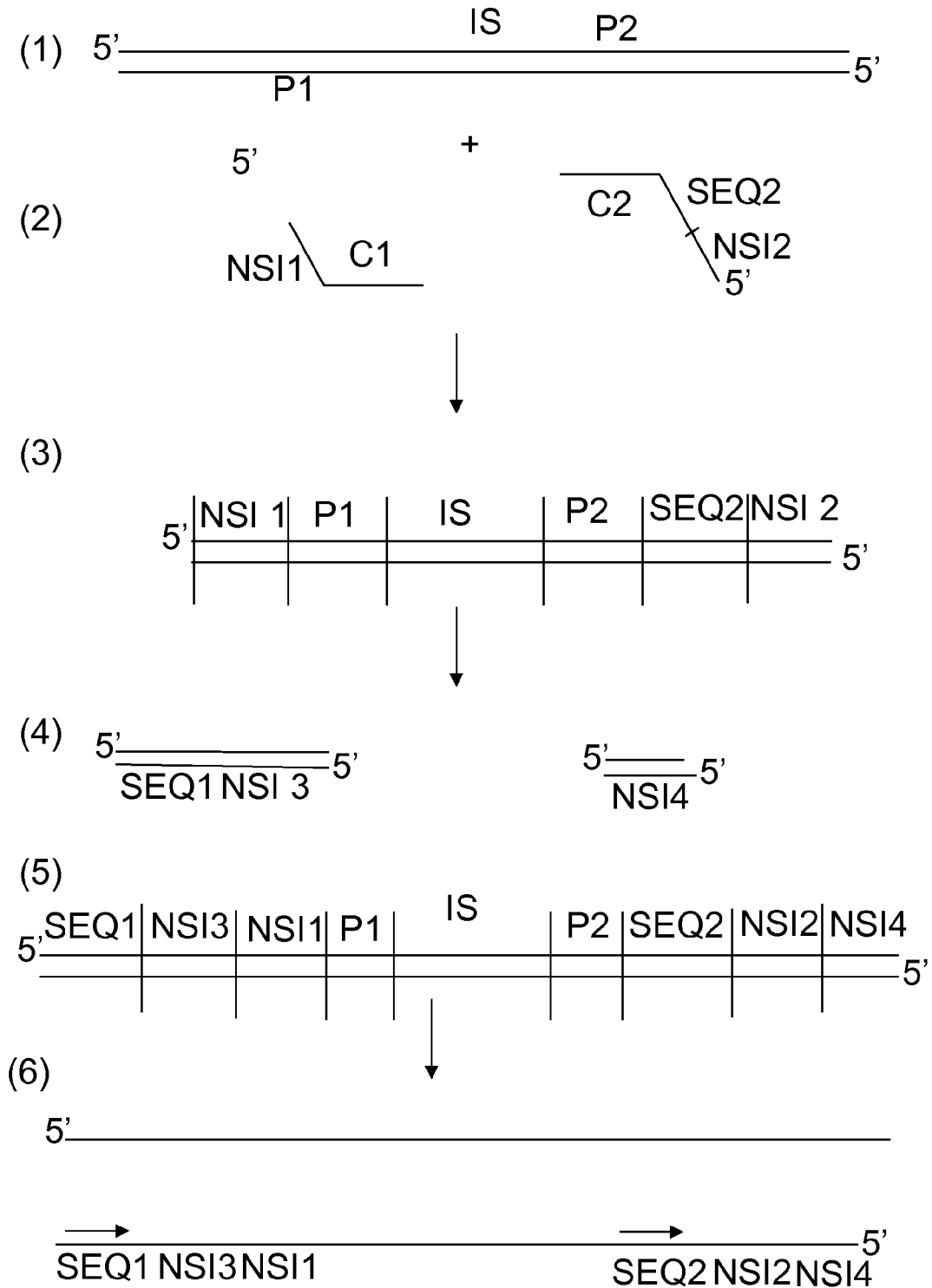

FIG. 9. Method for determining the sequence of four nucleotide sequence identifiers of an amplicon from a sample DNA: single-read double-tagging.

A sample DNA is provided (1) comprising an internal sequence (IS) flanked by two primer binding sites (P1 and P2), as well as a pair of amplification primers (2) comprising sequences complementary to a primer binding site at the 3'-end (C1 or C2). The primers comprise in addition NSIs and one of the primers comprises a sequencing primer binding site. The different primers comprising the different sections being represented as follows: 5'-NSI1-C1 and C2-SEQ2-NSI2-5'. The sample DNA is amplified with the amplification primers (3), resulting in an amplicon with two nucleotide sequence identifiers on the one outer ends of the amplicon. Next, a pair of adapters is provided (4). One adapter comprises a sequencing primer binding site (SEQ1) and an NSI (NSI3), the other primer comprises an NSI (NSI4). The adapters are ligated to either ends of the amplicon, resulting in an adapter ligated amplicon, wherein the SEQ1 section is on the outer end of the adapter ligated amplicon (5), and SEQ1 and SEQ2 are flanking the IS. One strand of the adapter ligated DNA fragment may serve as a template for sequencing using the SEQ1 and SEQ2 sequencing primer binding sites in two different sequencing reactions, i.e. using the corresponding different sequencing primers. The template strand used is represented as follows: 3'-SEQ1-NS13-NSI1-IS-SEQ2-NS12-NSI4-5'. (5' indicates the 5'-end of a nucleotide strand).

Figure 10:
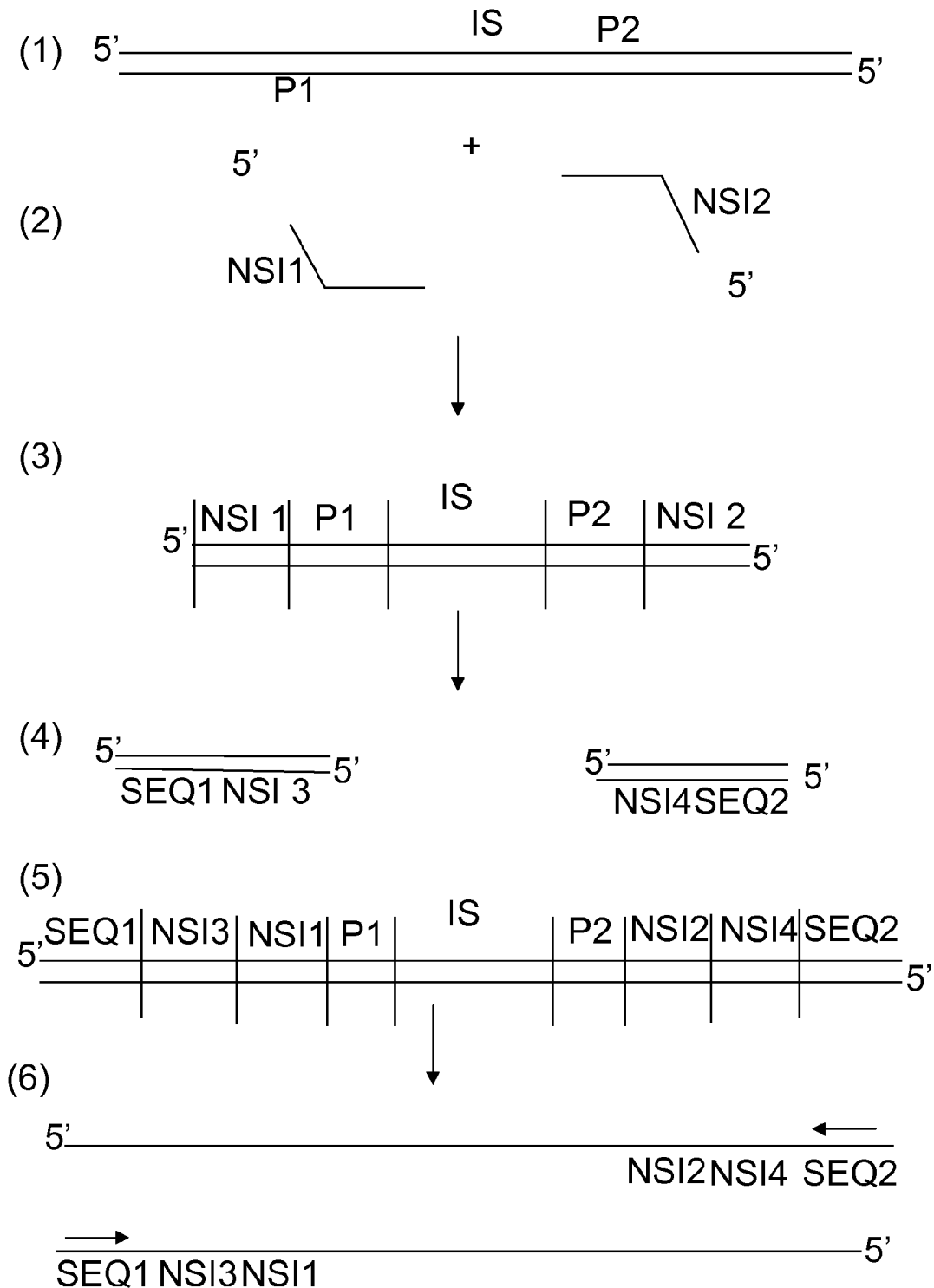

FIG. 10. Method for determining the sequence of four nucleotide sequence identifiers of an amplicon from a sample DNA.

A sample DNA is provided (1) comprising an internal sequence (IS) flanked by two primer binding sites (P1 and P2), as well as a pair of amplification primers (2) comprising sequences complementary to a primer binding site at the 3'-end (C1 or C2). The primers comprise in addition NSIs. The different primers comprising the different sections being as represented as follows: 5'-NSI1-C1 and C2-NSI2-5'. The sample DNA is amplified with the amplification primers (3), resulting in an amplicon with the two nucleotide sequence identifiers on the one outer ends of the amplicon. Next, a pair of adapters is provided (4). Each adapter comprises a sequencing primer binding site (SEQ1 or SEQ2) and an NSI (NSI3 or NSI4). The adapters are ligated to either ends of the amplicon, resulting in an adapter ligated amplicon, wherein the SEQ1 and SEQ2 sections are on the outer ends of the adapter ligated amplicon (5). Each strand of the adapter ligated amplicon may serve as a template for a sequencing reaction. Sequencing primers are provided such that from each template the NSI sequence(s) are determined. The sequences may be determined separately. The sequences may be determined consecutively, e.g. such as in paired-end sequencing. One of the template strands used is represented as follows: 3'-SEQ1-N513-NSI-1-P1-IS-P2-NS12-NSI4-SEQ2-5', for which a sequencing primer is used against SEQ1. (5' indicates the 5'-end of a nucleotide strand).

Figure 11:
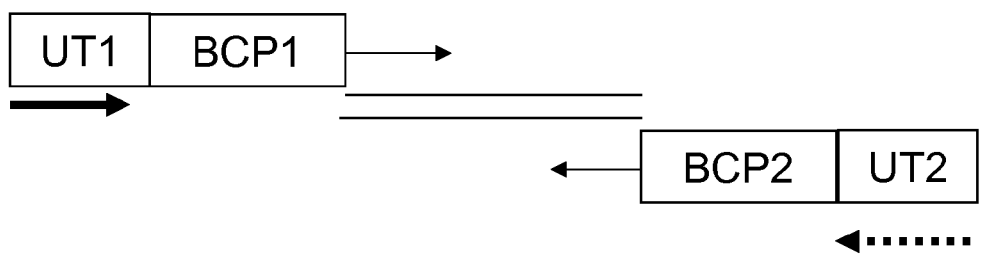
Figure 11:
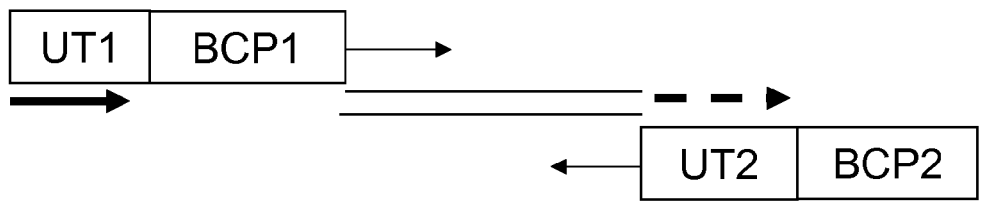

FIG. 11. Amplification with primer pair. (UT1, universal tail 1; BC1, barcode part 1, UT2 universal tail 2; BCP2, barcode part 2)

A. The universal tail 1 may be the sequence primer site 1 (heavy black arrow) and universal tail 2 may be the sequence primer site 2 (stippled arrow), e.g. P5 and P7 in case of Illumina GA paired-end sequencing.

B. The universal tail 1 may be the sequence primer site 1 (heavy black arrow) and universal tail 2 may be the sequence primer site 2 (dashed arrow), e.g. P5 and P7 in case of Illumina GA sequencing with two primer events from the same strand FIG. 12. Ligation of a pair of barcoded adaptors. (P5, P5+seq.pr.site; BC1, barcode part 1; BC2, barcode part 2; P7, P7+seq.pr.site; B, blunt end adapter).

A. Ligation of EcoRI and MseI barcoded adapters to EcoRI/MseI digested DNA, where the combination of barcode parts 1 (EcoRI side) and 2 (MseI side) define the sample uniquely.

B. Ligation of EcoRI and blunt end barcoded adapters to sample that was first digested with EcoRI, followed by EcoRI barcoded adapter ligation (barcode 1), followed by fragmentation of adapter-ligated fragments, optional end polishing and followed by blunt end adapter ligation (barcode part 2), where the combination of barcode parts 1 (EcoRI side) and barcode part 2 (blunt end side) define the sample uniquely.

DEFINITIONS

In the following description and examples, a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

As used herein, the singular forms "a," "an" and "the" include plural referents unless the context clearly dictates otherwise. For example, isolating DNA includes isolating a plurality of DNA molecules (e.g. 10's, 100's, 1000's, 10's of thousands, 100's of thousands, millions, or more molecules).

A "nucleotide sequence" according to the present invention may include any polymer or oligomer of nucleotides such as pyrimidine and purine bases, preferably cytosine, thymine, and uracil, and adenine and guanine, respectively and combinations thereof (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogenous in composition, and may be isolated from naturally occurring sources or may be artificially or synthetically produced. In addition, a nucleotide sequence may be DNA or RNA, or a mixture thereof, and may exist permanently or transitionally in single-stranded or double-stranded form, including homoduplex, heteroduplex, and hybrid states.

A "sample DNA" according to the invention is a sample which is derived from an organism and which comprises DNA. A "sample DNA" may comprise cells from an organism which comprises DNA, but also isolated DNA from the cells from an organism. As long as the "sample DNA" comprises DNA that can be used in the method of the invention such a sample DNA may be used in the invention. Organisms from which sample DNA may be obtained are for example plants, mammals, fungi, and microorganisms. Sample DNA may also comprise expressed sequence tags or cDNA, wherein RNA as it is expressed in cells of organisms is converted into double stranded DNA via reverse transcription. The sample DNA may also comprise pooled sample DNAs obtained from different sites of an organism, and/or from several different organisms. Pooled sample DNAs may be pooled e.g. in a 3-D pooling scheme such that the origin of each sample that is comprised in a sample DNA may be determined (e.g. as described in WO2007/037678).

"Fragmenting DNA" includes any technique that, when applied to a sample DNA, results in DNA fragments. Techniques well known in the art are sonication, shearing and/or enzymatic restriction, but other techniques can also be envisaged.

A "restriction endonuclease" or "restriction enzyme" is an enzyme that recognizes a specific nucleotide sequence (recognition site), e.g. in a double-stranded DNA molecule, and will cleave both strands of the DNA molecule at or near every recognition site, leaving a blunt or a 3'- or 5'-overhanging end. The specific nucleotide sequence which is recognized may determine the frequency of cleaving, e.g. a nucleotide sequence of 6 nucleotides occurs on average every 4096 nucleotides, whereas a nucleotide sequence of 4 nucleotides occurs much more frequent, on average every 256 nucleotides. Type I restriction enzymes cut at a site that differs, and is some distance (at least 1000 bp) away, from their recognition site. The recognition site is asymmetrical and is composed of two portions—one containing 3-4 nucleotides, and another containing 4-5 nucleotides—separated by a spacer of about 6-8 nucleotides. Type II restriction enzymes have recognition sites that are usually undivided and palindromic and 4-8 nucleotides in length. They recognize and cleave DNA at the same site. Type IIs cut outside their recognition sequence and Type IIB cleaves DNA on both sides of their recognition site to cut out the recognition site. Type III restriction enzymes (e.g. EcoP15) recognize two separate non-palindromic sequences that are inversely oriented. They cut DNA about 20-30 base pairs after the recognition site. Type IV restriction enzymes cut methylated DNA.

"Polishing" includes any technique used to make double stranded nucleotide sequences which may have 3' or 5' overhangs blunt ended. For example, in case a sample DNA is fragmented using sonication or using enzymes which result in staggered (overhanging) ends. DNA Polymerase I, Large (Klenow) Fragment can be used to fill in 5' overhangs (also called 3' recessed ends) and chew back 3' overhangs or Mung Bean Nuclease can be used to chew back 3' or 5' overhangs.

"Ligating" according to the invention involves the joining of separate double stranded nucleotide sequences. The double stranded DNA molecules may be blunt ended, or may have compatible overhangs (sticky overhangs) such that the overhangs can hybridise with each other. The joining of the DNA fragments may be enzymatic, with a ligase enzyme, DNA ligase. However, a non-enzymatic ligation may also be used, as long as DNA fragments are joined, i.e. forming a covalent bond. Typically a phosphodiester bond between the hydroxyl and phosphate group of the separate strands is formed in a ligation reaction. Double stranded nucleotide sequences may have to be phosphorylated prior to ligation.

"Amplification primers" refer to single stranded nucleotide sequences which can prime the synthesis of DNA. DNA polymerase cannot synthesize DNA de novo without primers. An amplification primer hybridises to the DNA, i.e. base pairs are formed. Nucleotides that can form base pairs, that are complementary to one another, are e.g. cytosine and guanine, thymine and adenine, adenine and uracil, guanine and uracil. The complementarity between the amplification primer and the existing DNA strand does not have to be 100%, i.e. not all bases of a primer need to base pair with the existing DNA strand. The sequence of the existing DNA strand, e.g. sample DNA or an adapter ligated DNA fragment, to which an amplification primer (partially) hybridises is often referred to as primer binding site (PBS). From the 3'-end of a primer hybridised with the existing DNA strand, nucleotides are incorporated using the existing strand as a template (template directed DNA synthesis). We may also refer to the synthetic oligonucleotide molecules which are used in an amplification reaction as "primers". The newly synthesized nucleotide sequences in the amplification reaction may be referred to as being an internal sequence. In case a PCR reaction is performed, the internal sequence typically is the sequence in between the two primer binding sites. According to the invention, a primer can be used in an amplification step to introduce additional sequences to the DNA. This can be achieved by providing primers with additional sequences such as an identifier, a sequencing adapter or a capturing ligand such as a biotin moiety. Modifications can be introduced by providing them at the 5' end of the primer, upstream from the part of the primer that sources to prime the synthesis of DNA.

"Amplification" or "amplifying" refers to a polynucleotide amplification reaction, namely, a population of polynucleotides that are replicated from one or more starting sequences. Amplifying may refer to a variety of amplification reactions, including but not limited to polymerase chain reaction (PCR), linear polymerase reactions, nucleic acid sequence-based amplification, rolling circle amplification and like reactions. Typically, amplification primers are used for amplification, the result of the amplification reaction being an amplicon.

"Sequencing primers" refer to single stranded nucleotide sequences which can prime the synthesis of DNA and are used to sequence DNA. An amplification primer may also be used as a sequencing primer. A sequencing primer can be used as an amplification primer. DNA polymerase cannot synthesize DNA de novo without primers. A sequencing primer hybridises to the DNA, i.e. base pairs are formed. Nucleotides that can form base pairs, that are complementary to one another, are e.g. cytosine and guanine, thymine and adenine, adenine and uracil, guanine and uracil. The complementarity between the amplification primer and the existing DNA strand does not have to be 100%, i.e. not all bases of a primer need to base pair with the existing DNA strand. The sequence of the existing DNA strand, e.g. sample DNA or an adapter ligated DNA fragment, to which a sequencing primer (partially) hybridises is often referred to as sequencing primer binding site (SEQ). From the 3'-end of a sequencing primer hybridised with the existing DNA strand, nucleotides are incorporated using the existing strand as a template (template directed DNA synthesis). The incorporation of a particular nucleotide (A, T, C, or G) can be detected during the synthesis, e.g. in pyrosequencing or when fluorescently labelled nucleotides are used. Alternatively, a chain termination method can be used, e.g. Sanger sequencing or Dye termination sequencing. In any case, these and other methods may be contemplated, as long as the order of the nucleotides of a DNA template may be determined by synthesizing DNA with a sequencing primer and detecting incorporated nucleotides and/or synthesised fragments.

"Sequencing" refers to determining the order of nucleotides (base sequences) in a nucleic acid sample, e.g. DNA or RNA. Many techniques are available such as Sanger sequencing and High Throughput Sequencing technologies (HTS). Sanger sequencing may involve sequencing via detection through (capillary) electrophoresis, in which up to 384 capillaries may be sequence analysed in one run. High throughput sequencing involves the parallel sequencing of thousands or millions or more sequences at once. HTS can be defined as Next Generation sequencing, i.e. techniques based on solid phase pyrosequencing or as Next-Next Generation sequencing based on single nucleotide real time sequencing (SMRT) .HTS technologies are available such as offered by Roche, Illumina and Applied Biosystems (Life Technologies). Further high throughput sequencing technologies are described by and/or available from Helicos, Pacific Biosciences, Complete Genomics, Ion Torrent Systems, Oxford Nanopore Technologies, Nabsys, ZS Genetics, GnuBio. Each of these sequencing technologies have their own way of preparing samples prior to the actual sequencing step. These steps may be included in the high throughput sequencing method. In certain cases, steps that are particular for the sequencing step may be integrated in the sample preparation protocol prior to the actual sequencing step for reasons of efficiency or economy. For instance, adapters that are ligated to fragments may contain sections that can be used in subsequent sequencing steps (so-called sequencing adapters). Or primers that are used to amplify a subset of fragments prior to sequencing may contain parts within their sequence that introduce sections that can later be used in the sequencing step, for instance by introducing through an amplification step a sequencing adapter or a capturing moiety in an amplicon that can be used in a subsequent sequencing step. Depending also on the sequencing technology used, amplification steps may be omitted.

An "adapter" is a short double-stranded DNA molecule with a limited number of base pairs, e.g. about 10 to about 100 base pairs in length, which are designed such that they can be ligated to the ends of DNA fragments or amplicons. Adapters are generally composed of two synthetic oligonucleotides which have nucleotide sequences which are at least partially complementary to each other. An adapter may have blunt ends, may have staggered ends, or a blunt end and a staggered end. A staggered end is a 3' or 5' overhang. When mixing the two synthetic oligonucleotides in solution under appropriate conditions, they will anneal to each other forming a double-stranded structure. After annealing, one end of the adapter molecule may be designed such that it is compatible with the end of a restriction fragment and can be ligated thereto; the other end of the adapter can be designed so that it cannot be ligated, but this does need not to be the case, for instance when an adapter is to be ligated in between DNA fragments. In certain cases adapters can be ligated to fragments to provide for a starting point for subsequent manipulation of the adapter-ligated fragment, for instance for amplification or sequencing. In the latter case, so-called sequencing adapters may be ligated to the fragments.

DETAILED DESCRIPTION OF THE INVENTION

In a first aspect of the invention, a use is provided of a combination of at least two nucleotide sequence identifiers in the preparation of a sample DNA for high throughput sequencing. Accordingly, a method is provided comprising a step in which a combination of at least two nucleotide sequence identifiers is used in the preparation of a sample DNA for high throughput sequencing. With the preparation of a sample DNA according thereto is meant that a sample DNA is prepared such that at least two NSIs are included in the sample DNA, i.e. the at least two NSIs are included e.g. in an amplicon and/or adapter ligated DNA fragment or amplicon thereof. The at least two NSIs are thus included in a nucleotide sequence of the sample DNA such that a single polynucleotide molecule comprises the at least two NSIs. The combination of the NSIs serves as unique identifiers ('split barcode') for the sample DNA.

From a design perspective, there is no practical limitation to the number of nucleotide sequence identifiers that one can use. For instance, one nucleotide may already serve as a nucleotide sequence identifier. Hence, 4 different nucleotide sequence identifier may be designed: A, G, C or T. The sequences flanking such a single nucleotide identifier may serve to guide the identification of the NSI. By increasing the size of a barcode, the number of possibilities increase. Three DNA bases allow for 64 possible 3-mer sequences ($4^3$), 256 possible 4-mers ($=4^4$), 1024 possible 5-mers ($=4^5$), and 4096 possible 7-mers ($=4^6$) etc. In practice, it may however be preferred to select a subset from these sequences to avoid the use in the same experiment of nucleotide sequence identifiers that differ by just one base (such as e.g. GATC and GATT in case of 4-mers), as this could result in a wrong assignment in case of a one base amplification- or sequencing error. Similarly, it may be preferred to avoid the use of nucleotide sequence identifiers that have two identical consecutive bases (e.g. AATGC having two consecutive A's in case of a 5-mer) because certain NGS platforms have higher error rates for so called "homopolymer" sequences. Despite such selection criteria, in general there is no shortage of suitable nucleotide sequence identifiers as the increment of their length with a base creates a four-fold higher starting number to select from.

Thus, when for example in a high throughput sequencing method of a prepared sample DNA the two NSI sequences are determined, the combination of the two NSIs determines the origin of prepared sample DNA. This way, the number of NSIs, and thus e.g. the number of different primers and/or adapters that has to be used can be reduced considerably. For example, for 100 samples, currently 100 NSIs are used, e.g. 100 different forward primers comprising the NSIs are combined with one reverse primer. According to the invention, by using a split barcode, 10 NSIs would suffice, and thus 10 different forward primers with 10 different reverse primers can be used of which 100 unique combinations can be made. Thus, the total number of primers that has to be used is reduced considerably, the number being reduced from 101 primers to 20 primers. Hence, reducing the complexity of the sample preparation workflow, increasing the likelihood of equal representation of samples, reducing the workload and required storage capacity and reducing the experimental costs.

In a further embodiment, the use is provided of a combination of at least two NSIs in the preparation of a sample DNA for high throughput sequencing, wherein in the high throughput sequencing a plurality of prepared sample DNAs is used, wherein each preparation of a sample DNA comprises a unique combination of the at least two NSIs wherein a first NSI is selected from a group of NSIs and a second NSI is selected from the group of NSIs.

The group of NSIs used comprises all NSIs. For each sample DNA, a nucleotide sequence identifier is selected from the group. This means that for a sample DNA for the at least two NSIs, the same NSI may be selected in the combination of NSIs. In addition, for a sample DNA for the at least two NSIs, different NSIs may be selected in the combination of NSIs. As long as the combination of the NSIs is unique for each sample DNA, such a combination may be used. The group of NSIs may also comprise at least two subgroups of NSIs, wherein each first and second NSI may be selected from a different subgroup. In addition to the first and second NSIs, further NSIs may be used selected from the group of NSIs. A group of NSIs may comprise at least 4, 10, 100 or 1000 NSIs.

It is understood that wherein throughout the invention a group of NSIs is provided, the group may be virtually provided, i.e. not physical. The group may for example be provided in silico and/or in physico. For example, a group of NSIs may be provided as a list of sequences. NSIs may be selected from that list and used for designing in silico a primer and/or adapter. It is thus understood that the subsequent steps of providing a group of NSIs and providing an adapter may comprise providing a group of NSIs in silico, selecting from that group an NSI in silico, designing an adapter in silico, and next providing in physico the adapter comprising the NSI. Alternatively, the NSIs may also be provided in physico and be used directly, for example, in a scenario wherein an adapter is used which consists of a nucleotide sequence identifier. Or for example, the NSIs may be provided in physico and be linked (e.g. ligated or otherwise) to other nucleotide strands such that an adapter and/or amplification primer is generated, thereby providing an adapter and/or amplification primer comprising an NSI.

The rationale of the invention is that a large number of unique combinations is created by using at least two different nucleotide sequence identifiers that are incorporated in each sample and exploiting the power of multiplication in order to reduce upfront reagent costs. This is shown in table 1 for a number of mathematically optimal situations for two NSis.

TABLE 1

Optimal combinations of NSIs with two NSIs.

| # of unique combinations (A) | # of different NSIs (B) | # of different NSIs (C) | # of different NSIs, B + C (D) | # of barcodes saved (A − D) |
|---|---|---|---|---|
| 100 | 10 | 10 | 20 | 80 |
| 1,024 | 32 | 32 | 64 | 960 |
| 4,096 | 64 | 64 | 128 | 3,968 |
| 16,384 | 128 | 128 | 256 | 16,128 |

As said, the concept is not limited to the examples shown in table 2 but other combinations can be considered as well. For example, less optimal combinations may be selected. Combinations which may involve more than two NSIs can be selected as well. For example, With 10 NSIs, and combining four NSIs, 10×10×10×10=10,000 unique combinations are possible. In the design and/or combination strategy used, practical considerations are also taken into account, e.g. practical considerations related to preparation of the sample DNA.

The prepared sample DNA is a sample DNA that has underwent processing by which the at least two nucleotide sequence identifiers are included in the DNA, i.e. the at least two NSIs are included in a DNA molecule comprising the two NSIs and a DNA sequence from the sample DNA. The DNA molecule may be a double stranded DNA molecule or a single stranded DNA molecule. It is understood that the prepared sample DNA may comprise a plurality of different DNA molecules, each DNA molecule comprising the unique combination of NSIs such that the each DNA molecule can be assigned to a sample DNA it originates from. In the high throughput sequencing method, of each of the DNA molecules from the plurality of DNA molecules a sequence may be determined with high throughput sequencing.

In one embodiment, the prepared sample DNA comprises an amplicon. For instance at least two NSIs are included in primers used to prepare an amplicon. The amplicon thus comprises at least two NSIs from the at least two different primers used. Amplicons may be prepared for instance in a PCR reaction. An amplicon may also be prepared from a nested PCR, i.e. preparing a first amplicon with a first set of primers in a first PCR reaction followed by a second PCR reaction with a second set of primers, which primers are different from the first set of primers and which primers amplify the amplicon of the first PCR reaction. A nested PCR may for example be performed to amplify DNA sequences which have a very low concentration, or may for example serve to provide an additional identifier or additional identifiers.

In one embodiment, the prepared sample DNA comprises an adapter ligated DNA fragment, sample DNA is fragmented and adapters ligated to the DNA fragments. At least two adapters are ligated to a DNA fragment, and each of the at least two adapters comprises a NSI.

In one embodiment, the prepared sample DNA comprises an amplicon and an adapter ligated fragment.

In one embodiment, the prepared sample DNA comprises an amplified adapter ligated fragment and/or an adapter ligated amplicon. For instance, a sample DNA may be subsequently subjected to fragmentation, adapter ligation, and amplification. Conversely, a sample DNA may for instance subsequently be subjected to amplification, fragmentation, and adapter ligation. In this embodiment, at least two of all the amplification primers and/or adapters used in the preparation of the sample DNA comprise an NSI.

In one embodiment, the method according to the invention comprises:

a) providing adapters and/or amplification primers, wherein at least a first adapter or amplification primer comprising a first nucleotide sequence identifier selected from the group of nucleotide sequence identifiers and a second adapter or amplification primer is provided comprising a second nucleotide sequence identifier selected from the group of nucleotide sequence identifiers, and wherein optionally, further adapter or amplification primers are provided comprising further nucleotide sequence identifier selected from the group of nucleotide sequence identifiers;

b) providing a plurality of sample DNAs;

c) performing ligation and/or amplification reactions on the sample DNAs using the adapters and/or amplification primers, to provide ligated and/or amplified sample DNA comprising the first, second and optionally further nucleotide sequence identifiers;

d) determining at least the sequence of the of first, second and further nucleotide sequence identifiers using high throughput sequencing;

e) determining the sample origin of the ligated and/or amplified sample DNAs.

As long as in the preparation of a sample DNA at least two NSIs are used which end up in a single DNA molecule comprising the two NSIs and a DNA sequence from the sample DNA, such a sample preparation method may be contemplated according to the invention. Thus, separate different adapter ligation steps and/or separate amplification steps may be combined in order to incorporate at least two NSIs in a prepared sample DNA. The preparation of a sample DNA may also comprise steps that do not involve the addition of NSIs.

It is understood that in the preparation of the sample DNA, steps that may be performed in the subsequent sequencing step may also be included and vice versa. Steps required for the subsequent sequencing step may also be included in the preparation of the sample DNA. For example, in a sequencing reaction, sequencing primers can be used that bind to sequencing primer binding sites present in a template. Hence, adapters and/or amplification primers used in the preparation of a sample DNA may comprise sequencing primer binding sites in addition. Alternatively, sequencing primer binding sites may be added in the high throughput sequencing method providing these additional sequences at a later stage.

In addition to the sequencing of the at least two NSIs in the high throughput sequencing method, sequences from the sample DNA may also be sequenced. Such sequences may also be referred to as internal sequences, as these are sequences which are captured and/or amplified with the sample DNA preparation method and may represent unknown sequences from sample DNAs that are of interest. These internal sequences may also be sequenced along with the NSIs, and thus the origin of the sample comprising these internal sequences can be determined by the combination of the NSIs. This way, for example polymorphisms may be detected between different samples, such as small nucleotide polymorphisms, deletions, insertions etc, by comparing the internal sequences and/or comparing the internal sequences with a reference sequence. Furthermore, these internal sequences may also assist in the assignment of different reads to a prepared sample DNA, for instance in the scenario as described below where different sequencing reads are used to build a contig.

High throughput sequencing involves the parallel sequencing of thousands or millions or more sequences at once. Whichever high throughput sequencing method used, the NSIs of the prepared sample DNAs are determined such that each combination of NSIs may be assigned to a prepared sample DNA. For example, contigs may be built by aligning and combining different sequencing reads by which the at least two NSIs may be coupled, and thus can be assigned to a single DNA molecule comprising the at least two NSIs. Also, two sequencing reactions may be performed on the complementary strands of a prepared sample DNA which is preferred in case the internal sequences of the fragment are required from both ends, when for instance the internal sequence is relatively large. When the two sequencing read can be assigned to the prepared sample DNA, comprising the at least two NSIs and a DNA sequence from the sample DNA, such high throughput sequencing methods can be contemplated. Also, the at least two NSIs may be determined from a single sequencing read in a high throughput sequencing method.

For example, in a so called paired-end sequencing method, in a first sequencing reaction a first sequence may be determined including an NSI using one of the strands as a template. After the first sequencing reaction, a complementary strand may be generated from the strand first used as a template. A second sequencing reaction can subsequently be performed using this newly generated strand as a second template. Thus, two DNA template strands are used in this method. For example, the structure of a first sequencing template strand can be 3'-Sequence primer binding site 1-NSI 1-internal sequence-reverse complement NSI 2-reverse complement sequence primer binding site 2-5'. After the first sequencing reaction, a reverse complement of the first sequencing template strand can be generated, which can subsequently be used in a second sequencing reaction. The second sequencing reaction thus having the following template: 3'-Sequence primer binding site 2-NSI 2-reverse complement internal sequence-reverse complement NSI 1-reverse complement sequence primer binding site 1-5'. Because both sequence reads co-localize (e.g. in the same well, the same bead), the two sequence reads comprising NSI 1 and NSI 2 can be assigned to the same prepared sample DNA and used to identify the prepared sample DNA. Such scenarios of sample preparation and subsequent sequencing are depicted in FIGS. 5, 7 and 10.

In one embodiment, in the high throughput sequencing method, a single DNA template of the prepared sample DNA is used. With a single DNA template according to the invention is meant a single stranded DNA molecule which comprise the at least two nucleotide sequence identifiers. It is understood that a single DNA template from a prepared sample DNA may comprise a plurality of single DNA template molecules, e.g. comprising different internal sequences derived from a sample DNA with each different internal sequence being linked with the unique combination of NSIs. When for example, the prepared sample DNA is an amplicon (or plurality of amplicons), the amplicon comprises two strands of DNA. In this embodiment, only one of the strands of an amplicon is used in the sequencing reaction to determine the NSI sequences. This way, the origin of a prepared sample DNA can be determined without requiring building a contig and/or without requiring a sequence derived from another DNA template. NSIs may flank the internal sequence of the prepared sample DNA. NSIs may also be on one side of (an internal sequence of) a prepared sample DNA. In these scenarios, a single DNA template molecule of a prepared sample DNA can have the following structure: 3'-Sequence primer binding site-NSI 1-internal sequence-NSI 2-5' or 3'-Sequence primer binding site-NSI 1-NSI 2-internal sequence-5'. The prepared sample DNA may comprise additional sequences. The order of the sequence primer binding site, NSIs, and internal sequence is what is of interest in this structural representation. The sequence primer binding site may be incorporated during the preparation of a sample DNA and/or may be incorporated in the high throughput sequencing method. The length and/or quality of sequences generated in high throughput sequencing may be limited. On the other hand, the sequencing length may be restricted such that both NSIs flanking the internal sequence can not be determined. It may be advantageous to have the NSIs on one side of the internal sequence, i.e. the part of the single DNA template that is sequenced first, such that both sequences can be determined in a single read. The NSIs may also be on both sides of the internal sequence.

In one embodiment, the single DNA template used may comprise two sequencing primer binding sites, wherein each sequencing primer binding site is located 3' of a different nucleotide sequence identifier. In general, a single DNA template may comprise a first section and a second section, with an internal sequence derived from the sample DNA in between. The first section comprises a sequencing primer binding site with 5' located thereof an NSI and optional further NSIs, and the second section comprises a second sequencing primer binding site with 5' located thereof an NSI and optional further NSIs. In this scenario, a single DNA template of a prepared sample DNA can have the following structure: 3'-Sequence primer binding site 1-NSI 1-internal sequence-Sequence primer binding site 1 NSI 2-5'. The prepared sample DNA may comprise additional sequences. The order of the sequence primer binding sites, NSIs, and internal sequence is what is of interest in this structural representation. Thus, the sequencing primer binding site can be located directly 3' of a nucleotide sequence identifier but additional sequences may also be present between a sequencing primer binding site and a nucleotide sequence identifier. In this scenario, from a single template, two different sequencing reactions may be performed consecutively in the high throughput sequencing method. One sequencing reaction will determine one (or more) NSI, and a second sequencing reaction a second NSI (or more). The two sequencing reactions of this embodiment performed in a high throughput sequencing method using the same template may be referred to as "single-read double tagging" sequencing hereinafter. Such scenarios of single-read double tagging are depicted in FIGS. 6, 8 and 9.

During the sample preparation and/or during the high throughput sequencing method used, the different samples or part of the different samples may be pooled such that steps that may be performed simultaneously can be performed simultaneously. The sample origin may still be determined as no samples or part of different samples are pooled by which the sample origin may no longer be traced back. For example, in a scenario wherein in the preparation of a sample DNA, NSIs are added in different steps, it may be beneficial to pool at least part of samples under preparation after such a step. For example, in a scenario in which 6 NSIs are used for 36 samples, each sample DNA is first subjected to a step that adds one of 6 different NSIs (A-F). Samples that comprise unique identifiers may be pooled (A1, B1, C1, D1, E1, F1) and each pool may now undergo the addition of one of the 6 identifiers, each group of six having a unique second identifier (A2, B2, C2, D2, E2, or F2), whereby A1 and A2 etc. may or may not be identical. Finally, once all the sample DNAs have been prepared, prepared sample DNAs may be pooled (partially or as a whole) in any possible way, because the at least two unique identifiers are now incorporated.

Different methods are possible for identifying the sample origin of a prepared sample DNA comprising a unique combination of at least two NSIs.

In one embodiment of the invention, a method is provided for identifying the sample origin of amplicons from a plurality of sample DNAs comprising the steps of:
a) providing a plurality of sample DNAs;
b) providing a group of nucleotide sequence identifiers;
c) providing first amplification primers, each first primer comprising a first nucleotide sequence identifier selected from the group of nucleotide sequence identifiers;
d) providing second amplification primers, each second primer comprising a second nucleotide sequence identifier selected from the group of nucleotide sequence identifiers;
e) amplifying each sample DNA with a unique pair of a first and second amplification primer to give amplicons;
f) optionally, pooling at least part of the amplicons;
g) determining the sequence of the first identifier sequence and the second identifier sequence of the amplicons using high throughput sequencing;
h) determining the sample origin of the amplicons.
A scheme of the sample preparation of this method of this embodiment is shown in FIG. 1. In this method, two NSIs are included in a first and second amplification primer. The amplicon comprises the two NSIs. The amplification primers may be designed to amplify a particular internal sequence which is of interest. By sequencing at least part of the internal sequence and the two NSIs of the amplicon, each sequenced (partial) internal sequence may be assigned to a sample DNA from which is originates. Alternatively, the amplification primers may be designed such that they are selective towards a particular primer binding site. By determining only the sequence of the two NSIs the presence or absence of an amplicon for a particular sample DNA is determined. Amplification primers used may have phosphorylated 5'-ends that are suitable for ligation of adapters that may be used in a subsequent high throughput sequencing method. Alternatively, amplicons may be phosphorylated if required.

In one embodiment, a method is provided for identifying the sample origin of adapter ligated DNA fragments from a plurality of sample DNAs comprising the steps of:
a) providing a plurality of sample DNAs;
b) providing a group of nucleotide sequence identifiers;
c) providing first adapters, each first adapter comprising a first nucleotide sequence identifier selected from the group of nucleotide sequence identifiers;
d) providing second adapters, each second adapter comprising a second nucleotide sequence identifier selected from the group of nucleotide sequence identifiers;
e) fragmenting each sample DNA;
f) ligating a unique pair of a first and second adapter to each fragmented sample DNA to give adapter ligated DNA fragments;
g) optionally, pooling at least part of the adapter ligated DNA fragments;
h) determining the sequence of the first identifier sequence and the second identifier sequence of the adapter ligated DNA fragments using high throughput sequencing;
i) determining the sample origin of the adapter ligated DNA fragments.
A scheme showing the sample preparation of a method of this embodiment is shown in FIG. 2. In this method, two adapters are ligated to a DNA fragment. As shown in FIG. 2, the adapters may be ligated to either site of a fragment. This is in particular suitable for high throughput sequencing methods in which such adapter ligation strategies are used. Many strategies to ligate two different adapters to fragments are possible. For example, first the DNA may be fragmented with two restriction enzymes with two different recognition sites. This results in DNA fragments which have ends that are the result of one restriction enzyme, but also in fragments that have ends which are the result of the two restriction enzymes. When two different adapters are designed that can be ligated to the specific restriction ends of each end, adapter ligated fragments can be formed which comprise the two different adapters. In addition, adapter ligated fragments are formed which comprise two of the same adapter. Alternatively, DNA may for instance be fragmented with a single restriction enzyme followed by the ligation of compatible adapters thereto. Next, the adapter ligated fragment may be fragmented again but now with e.g. sonification. The fragment ends are next polished and to the polished ends blunt ended adapters are ligated. The result is a mixture of adapter ligated fragments, including adapter ligated fragments comprising the restriction enzyme compatible adapter and the blunt end compatible adapter. In both scenarios, adapter ligated fragments are formed which may comprise the two NSIs. Only of the adapter ligated fragments that comprise the two different adapters the sample origin can be determined, as it is the combination of the two NSIs that is required to determine the sample origin.

In one embodiment, a method is provided for identifying the sample origin of adapter ligated amplicons comprising the steps of:
a) providing a plurality of sample DNAs;
b) providing a group of nucleotide sequence identifiers;
c) providing first amplification primers;
d) providing second amplification primers;
e) amplifying a sample DNA with a pair of a first and second amplification primer to give amplicons;
f) optionally, pooling at least part of the amplicons of sample DNAs each amplified with a different primer pair;
g) optionally, fragmenting the amplicons;
h) providing first adapters, each first adapter comprising a first nucleotide sequence identifier selected from the group of nucleotide sequence identifiers;
i) providing second adapters, each second adapter comprising a second nucleotide sequence identifier selected from the group of nucleotide sequence identifiers;
j) optionally, providing further adapters, each adapter comprising further nucleotide sequence identifiers selected from the group of nucleotide sequence identifiers;
k) ligating the first adapter, to the (fragmented) amplicons;
l) optionally, pooling at least part of the adapter ligated amplicons from step k);
m) repeating the ligating step with the second and further adapters, each ligating step followed, optionally, by pooling at least part of the obtained adapter ligated amplicons;
n) determining the sequence of the first, second, and optional further identifier sequences of the adapter ligated amplicons obtained in step m) using high throughput sequencing;
o) determining the sample origin of the adapter ligated amplicons.

In this embodiment, each sample DNA is subjected to at least one PCR amplification reaction. Multiple PCR reactions may be performed on each sample, for example for different target sequences. These different amplicons of each sample may optionally be pooled. The NSIs in this embodiment may be added in separate steps and after each step, at least part of the adapter ligated amplicons may pooled.

In other embodiments, ligating adapters and amplifying are combined, wherein the sample origin of a prepared sample DNA can be determined by determining 2-4 NSIs of a prepared sample DNA.

In one embodiment, a method is provided for identifying the sample origin of amplified adapter ligated DNA fragments from a plurality of sample DNAs comprising the steps of:
a) providing a plurality of sample DNAs;
b) providing a group of nucleotide sequence identifiers;
c) providing first adapters, each first adapter comprising a first nucleotide sequence identifier selected from the group of nucleotide sequence identifiers;
d) providing second adapters, each second adapter optionally comprising a second nucleotide sequence identifier selected from the group of nucleotide sequence identifiers;
e) fragmenting each sample DNA;
f) ligating at least a first adapter and optionally a second adapter to the fragmented sample DNA to give adapter ligated DNA fragments;
g) optionally, pooling at least part of the adapter ligated DNA fragments;
h) providing first amplification primers, each first primer comprising a third nucleotide sequence identifier selected from the group of nucleotide sequence identifiers;
i) optionally, providing second amplification primers, each second primer optionally comprising a fourth nucleotide sequence identifier selected from the group of nucleotide sequence identifiers;
j) amplifying the adapter ligated DNA fragments with a first amplification primer and optionally a second amplification primer, wherein the combination of a first, optional second, third and optional fourth NSI is unique for each sample, to give amplified adapter ligated DNA fragments;
k) optionally, pooling at least part of the amplified adapter ligated DNA fragments;
l) determining the sequence of the first, optional second, third and optional fourth identifier sequence of the amplified adapter ligated DNA fragments using high throughput sequencing;
m) determining the sample origin of the amplified adapter ligated DNA fragments.

A scheme of the sample preparation of a method of this embodiment is shown in FIG. 3. In this scenario, adapter ligated fragments may be prepared as described above. Alternatively, only one adapter may have been ligated to the fragments. The adapter(s) may comprise(s) in addition to an NSI, a primer binding site that may be used in a subsequent amplification and preferably a sequencing primer binding site. In the scenario where the same adapter is used on either side of a fragment, the same amplification primer may be used to amplify the adapter ligated fragment. The primer binding site may also include (part of) the NSI. Alternatively, (more) selective primers may be used that require additional (different) complementary nucleotides to the internal sequence of the DNA fragment beyond the restriction recognition site sequence of the internal sequence. The concept of selective primers is for example well described in WO2006/137733, and the method of this embodiment may involve preparation of sample DNA that uses such selective primers. For example, a primer is designed such that is complementary to (part of) the adapter sequence and the internal sequence of the sample DNA to which the adapter is ligated that comprises the restriction recognition site, and an additional nucleotide. The additional nucleotide is the selective nucleotide that renders the primer selective. On average, to one in four adapter ligated restriction fragments, the selective primer may bind and have the 3'-end extended. The concept of selective primers is well known from AFLP (EP 534858) as a complexity reduction method.

In any case, the end result is an amplified adapter ligated fragment, which may comprise at least two NSIs, or even 3 or 4 NSI. Including more NSIs may be advantageous as this may reduce the number of NSIs even further. For example, wherein for 10,000 samples, 100 NSIs are required in a combination of two NSIs (100×100), 10 NSIs are required in a combination of four NSIs (10×10×10×10).

In one embodiment, a method is provided for identifying the sample origin of adapter ligated amplicons comprising the steps of:
a) providing a plurality of sample DNAs;
b) providing a group of nucleotide sequence identifiers;
c) providing first amplification primers, each first primer comprising a first nucleotide sequence identifier selected from the group of nucleotide sequence identifiers;
d) providing second amplification primers, each second primer optionally comprising a second nucleotide sequence identifier selected from the group of nucleotide sequence identifiers;
e) amplifying each sample DNA with a pair of a first and second amplification primer to give amplicons;

f) optionally, pooling at least part of the amplicons of sample DNAs each amplified with a different primer pair;
g) optionally, fragmenting the amplicons;
h) providing first adapters, each first adapter comprising a third nucleotide sequence identifier selected from the group of nucleotide sequence identifiers;
i) optionally, providing second adapters, each second adapter comprising optionally a fourth nucleotide sequence identifier selected from the group of nucleotide sequence identifiers;
j) ligating at least a first adapter and optionally a second adapter to the (fragmented) amplicons, wherein the combination of a first, optional second, third and optional fourth nucleotide sequence identifier is unique for each sample, to give adapter ligated amplicons;
k) optionally, pooling at least part of the adapter ligated amplicons;
l) determining the sequence of the first, optional second, third and optional fourth identifier sequences of the adapter ligated amplicons using high throughput sequencing;
m) determining the sample origin of the adapter ligated amplicons.

A scheme of the sample preparation of a method of this embodiment shown in FIG. 4. In this scenario, a sample DNA may be subjected to amplification as described above, wherein now at least one of the primers comprises a NSI. The amplicon may be used directly (with or without polishing), and an adapter may be ligated to the amplicon. In this scenario, the adapter ligated amplicon will comprise on either end the same adapter. This adapter ligated amplicon may be subjected to further fragmentation and adapter ligation to a second adapter to obtain adapter ligated amplicons that have two different adapters. Alternatively, an amplicon may be subjected to a fragmenting step that results in fragments with two different ends that are compatible with two different adapters. In any case, an adapter ligated amplicon is formed which comprises 2-4 NSIs.

In one embodiment, in a method according to any of the methods as described above, in the step of determining the sequence of the identifier sequences using high throughput sequencing, the sequence of the identifier sequences is determined from a single DNA template of the prepared sample DNA. It is understood that the prepared sample DNA in the methods above comprises amplicons, adapter ligated fragments, adapter ligated amplicons and/or amplified adapter ligated fragments.

In one embodiment, in the single DNA template, the first second and optional further identifier sequences are at least 3' or 5' of an internal sequence. Of the prepared sample DNA, from which the sequence identifier sequences are determined from a single DNA template of the prepared sample DNA, the combination of identifier sequences required to uniquely identify the sample origin is at least either 3' or 5' of the internal sequence. A DNA sequencing template can thus be prepared which will have the identifier sequences flanked by the sequence primer binding site and the internal sequence. For example, the 3' end of such a DNA sequencing template may be represented by the following scheme: '3-SEQ1-NSI4-NSI3-NSI2-NS1I-IS- (etc.). This way, when the sequence of the template is determined, all the sequence identifiers are determined first. Such DNA templates may be generated by only adding sequence identifiers on one end of the internal sequence. For example, by adding adapters to only one end of a DNA fragment, and/or by using asymmetric adapters, or by using amplification primer sets wherein only one primer comprises a sequence identifier. Alternatively, adapters and/or amplification primers may be added to both 5' and 3' end of the DNA fragment, such that at both ends all the sequence identifiers are located. Such a DNA template may be represented by the following scheme '"3-SEQ1-NSI4-NSI3-NSI2-NS1I-IS-NSI1-NSI2-NSI3-NSI4-5'. Combinations of these different strategies are also possible, having in one or more separate steps an NSI added to both ends of the IS and to only one end. Such a DNA template may be represented by the following scheme '"3-SEQ1-NSI2-NSI1-IS-NSI1-5'. As long as a strategy is used wherein a DNA template is generated in which a unique combination of sequence identifiers is flanked by the sequence primer binding site and the internal sequence, such a DNA template will suffice. Thus, different combinations of amplification primers and/or adapters with and without nucleotide sequence identifiers can be used. For example, as shown in examples 3 and 4, when NSI2 and NSI4, which are optional, would correspond to NSI1 and NS3, suitable DNA templates are generated (i.e. it would still need to a sequence primer binding site, which may be added in a sample preparation for high through put sequencing). Similarly, the NSI2 and NSI4 sequences may not be included. Also, NSI2 may not be included, and the NSI4 corresponds to NS3, or NS12 may correspond to NSI1 and NSI4 is not included. In this scenario, only one end of the DNA template may comprise all of the NSIs. In a further embodiment, when the sequence of the identifier sequences is determined from a single DNA template of the prepared sample DNA, the single DNA template may comprise two sequencing primer binding sites, wherein each sequencing primer binding site is located 3' of a different nucleotide sequence identifier, and wherein in the high throughput sequencing method two different sequencing reactions are performed with two sequencing primers from the two sequencing primer binding sites of the single DNA template. The two different sequencing primer binding sites and corresponding 5' NSI or NSIs can be flanking an internal sequence of a prepared sample DNA. A prepared sample DNA may be an amplicon, adapter ligated fragment, adapter ligated amplicons and/or amplified adapter ligated fragment as described above.

In one embodiment, the single DNA template comprises two sequencing primer binding sites, wherein at least one sequencing primer binding site is located 3' of the at least two nucleotide sequence identifiers, and wherein in the high throughput sequencing method two different sequencing reactions are performed with two sequencing primers from the two sequencing primer binding sites of the single DNA template.

In one embodiment, when the sequence of the identifier sequences is determined from a single DNA template of the prepared sample DNA, the single DNA template may comprise two sequencing primer binding sites, wherein each sequencing primer binding site is located 3' of one or more nucleotide sequence identifiers, and wherein in the high throughput sequencing method two different sequencing reactions are performed with two sequencing primers from the two sequencing primer binding sites of the single DNA template. The two different sequencing primer binding sites and corresponding 5' NSI or NSIs can be flanking an internal sequence of a prepared sample DNA. Each of the one or more nucleotide sequence identifiers may be the same. Such a configuration may be represented as follows: '-3'-SEQ1-NS1-NS2-IS-SEQ2-NS1-NS2-5'. This way, by sequencing from a single template both unique combinations of unique identifiers are sequenced twice. Such a prepared sample DNA may be an amplicon, adapter ligated fragment, adapter ligated amplicons and/or amplified adapter ligated fragment as described above.

In one embodiment, when the sequence of the identifier sequences is determined from a single DNA template of the prepared sample DNA, the single DNA template may comprise two sequencing primer binding sites, wherein one sequencing primer binding site is located 3' of two or more nucleotide sequence identifiers, and wherein the other sequencing primer binding site may be located adjacent to the internal sequence. In the high throughput sequencing method two different sequencing reactions are performed with two sequencing primers from the two sequencing primer binding sites of the single DNA template. The two different sequencing primer binding sites and corresponding may be flanking an internal sequence of a prepared sample DNA. Such a configuration may be represented schematically as follows: '-3'-SEQ1-IS-SEQ2-NS1-N52-5'. This way, by sequencing from a single template in one sequencing run the internal sequence may be determined and in the other sequencing run the unique combination of sequence identifiers may be determined.

EXAMPLES

Example 1

Below, two different applications for sample preparation with split barcodes are exemplified, but other sample preparation methods which involve the incorporation of two different molecules to the sample fit within the scope of the invention too:
1) PCR amplification with two barcoded primers;
2) Adaptor ligation to a sample digested with two restriction enzymes or a sample digested with a single enzyme followed by adaptor ligation 1, followed by fragmentation and blunting the fragmented ends, followed by adaptor ligation 2.

PCR Amplification

A description is provided of the functional elements of a primer pair harboring split barcodes (barcode 1 and barcode 2), which are determined by either paired-end sequencing (A) or sequencing from the same strand with two priming events (B). A schematic view is provided in FIG. 11. It is observed in FIG. 11A that the universal tail 1 (bold arrow) may be the sequence primer site 1 (i.e. the primer site that is used in sequencing) and universal tail 2 (striped arrow) may be the sequence primer site 1 (i.e. the primer site that is used in sequencing), examples are P5 and P7 primers respectively as used in Illumina GA paired end sequencing. In FIG. 11B the universal tail 1 (bold arrow) may be the sequence primer site 1 (i.e. the primer site that is used in sequencing) and universal tail 2 (striped arrow) may be the sequence primer site 2 (i.e. the primer site that is used in sequencing), examples are P5 and P7 primers respectively as used in Illumina GA with two primer event from the same strand. The concept can be used any method involving amplification with a pair of primers. Examples thereof are amplicon sequencing (e.g. detection of mutations, natural polymorphisms), multiplexed SNP genotyping involving PCR primers such as KASP primers, Scorpions primers etc.

Adaptor Ligation

Figure 12:
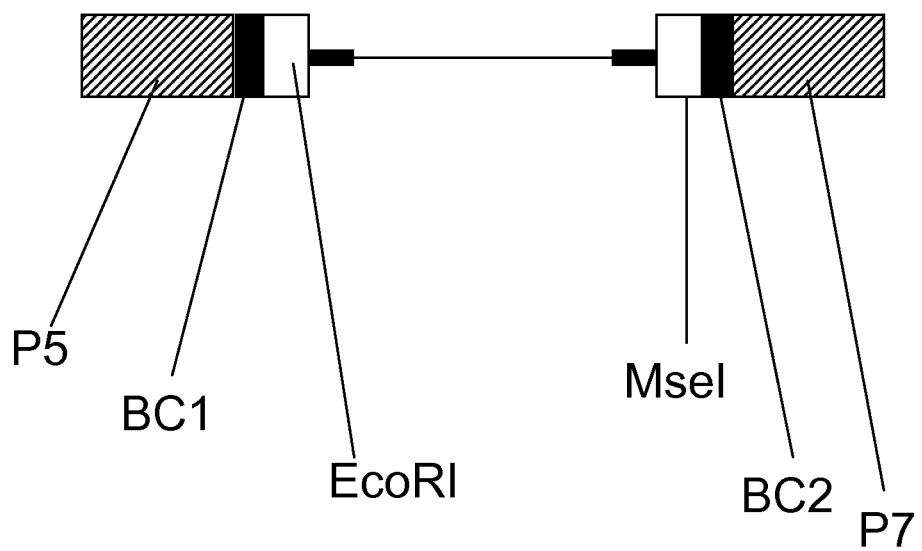
Figure 12:
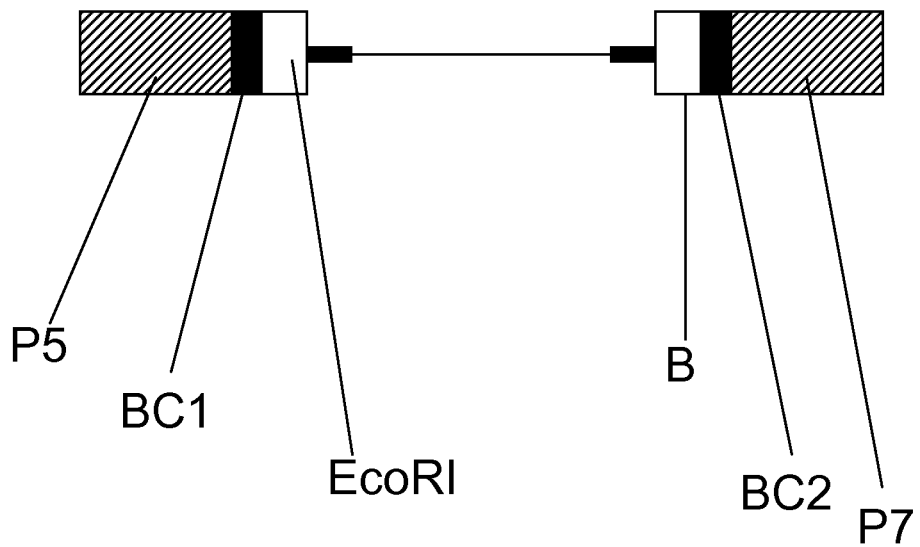

In a whole genome physical mapping experiment 480 different BAC pool samples were combined. This would require 480 different EcoRI barcoded adaptors. This amount of adaptors has been circumvented by using 80 EcoRI adaptors with 5 nt barcodes in combination with 6 MseI adaptors with 3 nt barcodes, which in combination generates 480 8-mer barcodes that are unique. In this case, sequencing was performed by performing two sequence primers events, as described in PCR amplification above and FIG. 11B. In FIG. 12, the general outline for the use of two barcoded adaptors is described in the context of Illumine GA sequencing (using P5 and P7 amplification and sequence primer regions). Part A describes sample preparation using two restriction enzymes to digest the DNA, while part B describes sample preparation using a combination of a restriction enzyme and blunt-end adaptor ligation. Alternative methods for sample preparation that involve the use of two barcoded adaptors are within the scope of the current invention. The concept can be used any method involving ligation of two adaptors, such as restriction fragment sequencing, AFLP, RAD, WGP, whole genome sequencing, paired-end sequencing, reduced representations sequencing etc.

The invention claimed is:

1. A method for identifying the sample origin of ligated and/or amplified sample DNA comprising:
   a) obtaining a plurality of first adapters or PCR amplification primers comprising first nucleotide sequence identifiers and second adapters or PCR amplification primers comprising second nucleotide sequence identifiers;
   b) performing ligation and/or PCR amplification reactions on sample DNAs of different origins using different combinations of the first and second adapters and/or PCR amplification primers, to provide ligated and/or amplified prepared sample DNAs each comprising the first and second nucleotide sequence identifiers in addition to the sequence captured and/or amplified from the sample DNA, wherein a unique combination of first and second nucleotide sequence identifiers is used for each sample DNA of each different origin;
   c) determining at least the sequence of the of first and second nucleotide sequence identifiers using high throughput sequencing;
   d) determining the sample origin of the ligated and/or amplified prepared sample DNAs based on the unique combination of first and second nucleotide sequence identifiers.

2. A method for identifying the sample origin of amplicons from a plurality of sample DNAs comprising the steps of:
   a) obtaining a plurality of first PCR amplification primers, each first PCR primer comprising a first nucleotide sequence identifier;
   b) obtaining a plurality of second PCR amplification primers, each second PCR primer comprising a second nucleotide sequence identifier;
   c) amplifying by PCR sample DNAs of different origins with different combinations of the first and second PCR amplification primers to give amplicons each comprising the first and second nucleotide sequence identifiers in addition to of the sequence amplified from the sample DNA, wherein a unique combination of first and second nucleotide sequence identifiers is used for each sample DNA of each different origin;
   d) optionally, pooling at least part of the amplicons;
   e) determining the sequence of the first identifier sequence and the second identifier sequence of the amplicons using high throughput sequencing;
   f) determining the sample origin of the amplicons based on the unique combination of first and second nucleotide sequence identifiers.

3. A method for identifying the sample origin of adapter ligated DNA fragments from a plurality of sample DNAs comprising the steps of:
   a) obtaining a plurality of different first adapters, each first adapter comprising a first nucleotide sequence identifier;
   b) obtaining a plurality of different second adapters, each second adapter comprising a second nucleotide sequence identifier;

c) ligating different combinations of the first and second adapters to fragmented sample DNAs of different origins to give adapter ligated DNA fragments each comprising the first and second nucleotide sequence identifiers in addition to the sequence captured from the sample DNA, wherein a unique combination of first and second nucleotide sequence identifiers is used for each sample DNA of each different origin;

d) optionally, pooling at least part of the adapter ligated DNA fragments;

e) determining the sequence of the first identifier sequence and the second identifier sequence of the adapter ligated DNA fragments using high throughput sequencing;

f) determining the sample origin of the adapter ligated DNA fragments based on the unique combination of first and second nucleotide sequence identifiers.

4. A method for identifying the sample origin of adapter ligated amplicons comprising the steps of:
 a) providing a plurality of sample DNAs;
 b) providing a group of nucleotide sequence identifiers;
 c) providing first PCR amplification primers;
 d) providing second PCR amplification primers;
 e) amplifying by PCR a sample DNA with a pair of a first and second PCR amplification primer to give amplicons;
 f) optionally, pooling at least part of the amplicons of sample DNAs each amplified with a different primer pair;
 g) optionally, fragmenting the amplicons;
 h) providing first adapters, each first adapter comprising a first nucleotide sequence identifier selected from the group of nucleotide sequence identifiers;
 i) providing second adapters, each second adapter comprising a second nucleotide sequence identifier selected from the group of nucleotide sequence identifiers;
 j) optionally, providing further adapters, each adapter comprising further nucleotide sequence identifiers selected from the group of nucleotide sequence identifiers;
 k) ligating the first adapter, to the (fragmented) amplicons to obtain amplicons each comprising the first nucleotide sequence identifier in addition to the sequence amplified from the sample DNA;
 l) optionally, pooling at least part of the adapter ligated amplicons from step k);
 m) repeating the ligating step with the second and further adapters, each ligating step followed, optionally, by pooling at least part of the obtained adapter ligated amplicons to obtain amplicons each comprising the second and optionally further nucleotide sequence identifiers in addition to the sequence amplified from the sample DNA;
 n) determining the sequence of the first, second, and optional further identifier sequences of the adapter ligated amplicons obtained in step m) using high throughput sequencing;
 o) determining the sample origin of the adapter ligated amplicons based on the unique combination of first, second and optionally further nucleotide sequence identifiers, wherein in steps k) and m) for each different sample DNA a unique combination of first, second and optionally further nucleotide sequence identifiers is used.

5. A method for identifying the sample origin of amplified adapter ligated DNA fragments from a plurality of sample DNAs comprising the steps of:
 a) providing a plurality of sample DNAs;
 b) providing a group of nucleotide sequence identifiers;
 c) providing first adapters, each first adapter comprising a first nucleotide sequence identifier selected from the group of nucleotide sequence identifiers;
 d) optionally, providing second adapters, each second adapter optionally comprising a second nucleotide sequence identifier selected from the group of nucleotide sequence identifiers;
 e) fragmenting each sample DNA;
 f) ligating at least a first adapter and optionally a second adapter to the fragmented sample DNA to give adapter ligated DNA fragments;
 g) optionally, pooling at least part of the adapter ligated DNA fragments;
 h) providing first PCR amplification primers, each first PCR primer comprising a third nucleotide sequence identifier selected from the group of nucleotide sequence identifiers;
 i) optionally, providing second PCR amplification primers, each second PCR primer optionally comprising a fourth nucleotide sequence identifier selected from the group of nucleotide sequence identifiers;
 j) amplifying by PCR the adapter ligated DNA fragments with a first PCR amplification primer and optionally a second PCR amplification primer, wherein the combination of a first, optional second, third and optional fourth nucleotide sequence identifier is unique for each sample, to give amplified adapter ligated DNA fragments each comprising the first, optional second, third and optional fourth nucleotide sequence identifiers in addition to the sequence captured from the sample DNA;
 k) optionally, pooling at least part of the amplified adapter ligated DNA fragments;
 l) determining the sequence of the first, optional second, third and optional fourth identifier sequence of the amplified adapter ligated DNA fragments using high throughput sequencing;
 m) determining the sample origin of the amplified adapter ligated DNA fragments based on the unique combination of first, optional second, third and optional fourth nucleotide sequence identifiers.

6. A method for identifying the sample origin of adapter ligated amplicons comprising the steps of:
 a) providing a plurality of sample DNAs;
 b) providing a group of nucleotide sequence identifiers;
 c) providing first PCR amplification primers, each first PCR primer comprising a first nucleotide sequence identifier selected from the group of nucleotide sequence identifiers;
 d) providing second PCR amplification primers, each second PCR primer optionally comprising a second nucleotide sequence identifier selected from the group of nucleotide sequence identifiers;
 e) amplifying by PCR each sample DNA with a pair of a first and second PCR amplification primer to give amplicons each comprising the first and optionally second nucleotide sequence identifier in addition to the sequence amplified from the sample DNA;
 f) optionally, pooling at least part of the amplicons of sample DNAs each amplified with a different primer pair;
 g) optionally, fragmenting the amplicons;
 h) providing first adapters, each first adapter comprising a third nucleotide sequence identifier selected from the group of nucleotide sequence identifiers;

i) optionally, providing second adapters, each second adapter comprising optionally a fourth nucleotide sequence identifier selected from the group of nucleotide sequence identifiers;

j) ligating at least a first adapter and optionally a second adapter to the (fragmented) amplicons, wherein the combination of a first, optional second, third and optional fourth nucleotide sequence identifier is unique for each sample, to give adapter ligated amplicons;

k) optionally, pooling at least part of the adapter ligated amplicons;

l) determining the sequence of the first, optional second, third and optional fourth identifier sequences of the adapter ligated amplicons using high throughput sequencing;

m) determining the sample origin of the adapter ligated amplicons based on the unique combination of first, optional second, third and optional fourth nucleotide sequence identifiers.

7. The method according to claim 1, wherein in the step of determining the sequence of the identifier sequences using high throughput sequencing, the sequence of the identifier sequences is determined from a single DNA template of the prepared sample DNA.

8. The method according to claim 7, wherein in the single DNA template, the first second and optional further identifier sequences are at least 3' or 5' of an internal sequence.

9. The method according to claim 8, wherein the single DNA template comprises two sequencing primer binding sites, wherein each sequencing primer binding site is located 3' of a different nucleotide sequence identifier, and wherein in the high throughput sequencing method two different sequencing reactions are performed with two sequencing primers from the two sequencing primer binding sites of the single DNA template.

10. The method according to claim 8, wherein the single DNA template comprises two sequencing primer binding sites, wherein at least one sequencing primer binding site is located 3' of the at least two nucleotide sequence identifiers, and wherein in the high throughput sequencing method two different sequencing reactions are performed with two sequencing primers from the two sequencing primer binding sites of the single DNA template.

11. The method according to claim 1 wherein the identifier does not contain two consecutive identical bases.

12. The method according to claim 1 wherein two identifiers differ by more than one nucleotide.

13. The method according to claim 1 wherein two identifiers differ by more than two nucleotides and do not contain two consecutive identical bases.

* * * * *

UNITED STATES PATENT AND TRADEMARK OFFICE
CERTIFICATE OF CORRECTION

PATENT NO. : 9,080,210 B2  
APPLICATION NO. : 13/702667  
DATED : July 14, 2015  
INVENTOR(S) : Michael Josephus Theresia Van Eijk and Henricus Johannes Adam Van Der Poel Page 1 of 1

It is certified that error appears in the above-identified patent and that said Letters Patent is hereby corrected as shown below:

Claims

Column 22 Claim 1, line 29: "c) determining at least the sequence of the of first and second nucleotide sequence…" should read -- c) determining at least the sequence of the first and second nucleotide sequence… --

Column 22 Claim 2, line 48: "c) …in addition to of the sequence amplified from the sample DNA…" should read -- c) …in addition to the sequence amplified from the sample DNA… --

Signed and Sealed this  
Sixteenth Day of February, 2016

Michelle K. Lee  
*Director of the United States Patent and Trademark Office*